United States Patent
Vormehr et al.

(10) Patent No.: US 12,153,041 B2
(45) Date of Patent: Nov. 26, 2024

(54) METHODS FOR PREDICTING THE USEFULNESS OF PROTEINS OR PROTEIN FRAGMENTS FOR IMMUNOTHERAPY

(71) Applicants: BioNTech SE, Mainz (DE); Tron-Translationale Onkologie an der Universitätsmedizin Der Johannesgutenberg-Universität Mainz, Mainz (DE)

(72) Inventors: Mathias Vormehr, Mainz (DE); Ugur Sahin, Mainz (DE); Barbara Schrörs, Mainz (DE); Martin Löwer, Bodenheim (DE); Sebastian Boegel, Obermoschel (DE)

(73) Assignees: TRON-Translationale Onkologie an der Universitätsmedizin der Johannes Gutenberg-Universität Mainz gGmbH, Mainz (DE); BioNTech SE, Mainz (DE)

( * ) Notice: Subject to any disclaimer, the term of this patent is extended or adjusted under 35 U.S.C. 154(b) by 372 days.

(21) Appl. No.: 16/301,019

(22) PCT Filed: May 10, 2017

(86) PCT No.: PCT/EP2017/061196
§ 371 (c)(1),
(2) Date: Nov. 13, 2018

(87) PCT Pub. No.: WO2017/194610
PCT Pub. Date: Nov. 16, 2017

(65) Prior Publication Data
US 2019/0178871 A1    Jun. 13, 2019

(30) Foreign Application Priority Data

May 13, 2016   (WO) ................ PCT/EP2016/060897

(51) Int. Cl.
| G01N 33/50 | (2006.01) |
| A61P 35/04 | (2006.01) |
| G01N 33/53 | (2006.01) |
| G01N 33/68 | (2006.01) |

(52) U.S. Cl.
CPC .......... *G01N 33/5035* (2013.01); *A61P 35/04* (2018.01); *G01N 33/5308* (2013.01); *G01N 33/6878* (2013.01); *G01N 33/6887* (2013.01); *G01N 2333/4712* (2013.01); *G01N 2800/52* (2013.01)

(58) Field of Classification Search
CPC .......... G01N 33/5035; G01N 33/5308; G01N 33/6878; G01N 33/6887; G01N 2333/4712; G01N 2800/52; A61P 35/04
See application file for complete search history.

(56) References Cited

U.S. PATENT DOCUMENTS

| 6,685,911 B1 | 2/2004 | Zitvogel et al. |
| 2004/0028692 A1 | 2/2004 | Zitvogel et al. |
| 2009/0280511 A1* | 11/2009 | Yahara ............... G01N 33/5011 435/7.23 |
| 2014/0178438 A1 | 6/2014 | Sahin et al. |

FOREIGN PATENT DOCUMENTS

| CA | 2486738 C | 7/2011 |
| CN | 1265038 A | 8/2000 |
| CN | 1250285 C | 4/2006 |
| JP | 2000-512161 A | 9/2000 |
| JP | 2009-273377 A | 11/2009 |
| WO | WO-99/03499 A1 | 1/1999 |
| WO | WO-02/05146 A2 | 1/2002 |
| WO | WO-2010/108215 A1 | 9/2010 |
| WO | WO-2012/159643 A1 | 11/2012 |
| WO | WO-2012/159754 A2 | 11/2012 |
| WO | WO-2015/063302 A2 | 5/2015 |
| WO | WO-2017/106638 A1 | 6/2017 |
| WO | WO-2017/194170 A1 | 11/2017 |
| WO | WO-2017/194610 A1 | 11/2017 |
| WO | WO-2018/195357 A1 | 10/2018 |
| WO | WO-2018/227030 A1 | 12/2018 |
| WO | WO-2019/050994 A1 | 3/2019 |
| WO | WO-2019/075112 A1 | 4/2019 |

(Continued)

OTHER PUBLICATIONS

Kuate et al. Exosomal vaccines containing the S protein of the SARS coronavirus induce high levels of neutralizing antibodies. (Virology 362: 26-37, 2007).*

Andre et al. Exosomes as Potent Cell-Free Peptide-Based Vaccine. I. Dendritic Cell-Derived Exosomes Transfer Functional MHC Class I/Peptide Complexes to Dendritic Cells (The Journal of Immunology 172:2126-2136, 2004).*

He et al. (Journal of Biomedicine and Biotechnology 2010, 26 pages, published online 2011).*

(Continued)

*Primary Examiner* — Alana Harris Dent
(74) *Attorney, Agent, or Firm* — Choate, Hall & Stewart LLP; Brenda Herschbach Jarrell; Rolando Medina

(57) ABSTRACT

The present invention relates to methods for predicting peptides or polypeptides such as T cell epitopes useful for immunotherapy such as for vaccination. In particular, the present invention relates to methods for predicting whether peptides or polypeptides such as tumor-associated antigens or epitopes, in particular tumor-associated neoantigens or neoepitopes, are immunogenic and, in particular, useful for immunotherapy such as for vaccination. The methods of the invention may be used, in particular, for the provision of vaccines which are specific for a patient's tumor and, thus, in the context of personalized cancer vaccines.

Figure 1:
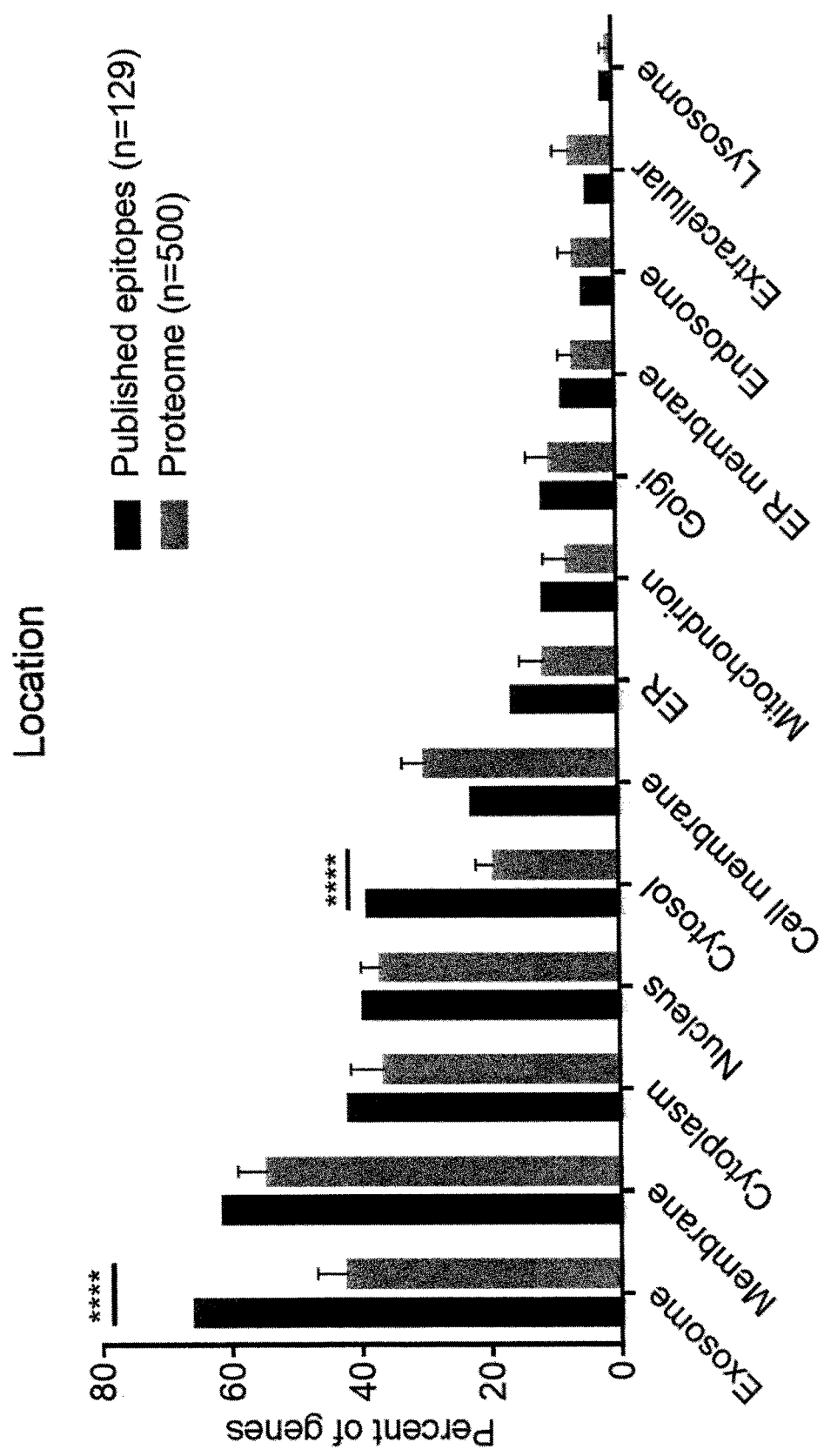

19 Claims, 2 Drawing Sheets
Specification includes a Sequence Listing.

(56) References Cited

FOREIGN PATENT DOCUMENTS

| WO | WO-2019/104203 A1 | 5/2019 |
| WO | WO-2019/168984 A1 | 9/2019 |

OTHER PUBLICATIONS

Garifulin et al. Application of serex-analysis for identification of human colon cancer antigens. Experimental Oncology 37(3): 173-180, Sep. 2015.*

Rajasagi et al. Systematic identification of personal tumor-specific neoantigensin chronic lymphocytic leukemia. Blood 124(3): 453-462, Jul. 17, 2014.*

International Preliminary Report on Patentability for PCT/EP2016/060897, received by the International Bureau of WIPO, 13 pages (Nov. 13, 2018).

International Preliminary Report on Patentability for PCT/EP2017/061196, received by the International Bureau of WIPO, 23 pages (Nov. 13, 2018).

International Search Report for PCT/EP2016/060897, received by the ISA/EP, 8 pages (Mar. 28, 2017).

Written Opinion for PCT/EP2016/060897, received by the ISA/EP, 12 pages (Mar. 28, 2017).

Written Opinion for PCT/EP2017/061196, received by the ISA/EP, 22 pages (Sep. 15, 2017).

International Search Report mailed Sep. 15, 2017 in corresponding International Application No. PCT/EP2017/061196.

Zeelenberg et al., "Antigen Localization Controls T Cell-Mediated Tumor Immunity," The Journal of Immunology; vol. 187; No. 3; Jun. 24, 2011; pp. 1281-1288.

Wolfers et al., "Tumor-derived exosomes are a source of shared tumor rejection antigens for CTL cross-priming," Nature Medicine; vol. 7; No. 3; Mar. 1, 2001; pp. 297-303.

Rimoldi, "Subcellular Localization of the Melanoma-associated Protein Melan-AMART-1 Influences the Processing of its HLA-A2-restricted Epitope," Journal of Biological Chemistry; vol. 276; No. 46; Sep. 10, 2001; pp. 43189-43196.

Koslowski et al., "A placenta-specific gene ectopically activated in many human cancers is essentially involved in malignant cell processes," Cancer Research; vol. 67; No. 19; Oct. 1, 2007; pp. 9528-9534.

Tureci et al., "Targeting the Heterogeneity of Cancer with Individualized Neoepitope Vaccines," Clinical Cancer Research; vol. 22; No. 8; Apr. 15, 2016; pp. 1885-1896.

Hacohen et al., "Getting Personal with Neoantigen-Based Therapeutic Cancer Vaccines," Cancer Immunology Research; vol. 1; No. 1; Apr. 7, 2013; pp. 11-15.

Andersen et al., "Increasing the efficacy of tumor cell vaccines by enhancing cross priming," Cancer Letters; vol. 325; No. 2; Dec. 1, 2012; pp. 155-164.

Srivastava, "Neoepitopes of Cancers: Looking Back, Looking Ahead," Cancer Immunology Research; vol. 3; No. 9; Sep. 1, 2015; pp. 969-977.

Wang et al., "Perspectives of SEREX-defined antigens in diagnosis and immunotherapy for gastric cancer," Cancer Biology & Therapy; vol. 3; No. 9; Sep. 27, 2004; pp. 806-811.

Boncheva et al., "New targets for the immunotherapy of colon cancer-does reactive disease hold the answer?" Cancer Gene Therapy; vol. 20; No. 3; Mar. 1, 2013; pp. 157-168.

Chen, "Cancer Immunity—SEREX Review—Classification," Journal of Cancer Immunity; Jan. 1, 2004; retrieved from the internet: http://archive.cancerimmunity.org/SEREX/classification.htm [retrieved on Aug. 25, 2017].

Behrends et al., "Novel tumor antigens identified by autologous antibody screening of childhood medulloblastoma CDNA libraries: SEREX-Defined Medulloblastoma Antigens," International Journal of Cancer, vol. 106; No. 2; Aug. 20, 2003; pp. 244-251.

Alsoe et al., "Identification of prostate cancer antigens by automated high-throughput filter immunoscreening," Journal of Immunological Methods; vol. 330; No. 1-2; Nov. 20, 2007; pp. 12-23.

Gillissen et al., "Donor-Derived B Cells Produce Potent AML-Specific ANtibodies that Recognize Novel Tumor- Specific Antigens and Mediate Graft-Versus-Leukemia Immunity," Blood; vol. 126; Jan. 1, 2015; retrieved from Internet: http://www.bloodjournal.org/content/126/23/3146?ss0-checked=true [retrieved on Aug. 28, 2017].

Manabu et al., "Antigens recognized by IgG derived front tumor-infiltrating B lymphocytes in human lung cancer," Anticancer Research; vol. 26; No. 5A; Sep. 1, 2006; pp. 3607-3611.

Brown, "Immunology: Actin' dangerously," Nature; vol. 485; No. 7400; May 31, 2012; pp. 589-590.

Jin et al., "Immunomodulatory Effects of dsRNA and its Potential as Vaccine Adjuvant," Journal of Biomedicine and Biotechnology; vol. 6; No. 1; Jan. 1, 2010; pp. 148-217.

Salio et al., "Viral Immunity: Cross-Priming with the Help of TLR3," Current Biology; vol. 15; No. 9; May 1, 2005; pp. R336-R339.

Ehrlich, D. et al., Intratumoral anti-HuD immunotoxin therapy for small cell lunch cancer and neuroblastoma, Journal of Hematology & Oncology, 7(91): 8 pages (2014).

Van Montfoort, N. et al., Understanding MHC class I presentation of viral antigens by human dendritic cells as a basis for rational design of therapeutic vaccines, Frontiers in Immunology, 5(182): 14 pages (2014).

Gubin, M. M., et al., Tumor neoantigens: building a framework for personalized cancer immunotherapy, The Journal of Clinical Investigation, 125(9):3413-3421 (2015).

Sahin, U., et al., Human neoplasms elicit multiple specific immune responses in the autologous host, Proc. Natl. Acad. Sci., 92:11810-11813 (1995).

* cited by examiner

SEQUENCE LISTING

```
<160> NUMBER OF SEQ ID NOS: 2

<210> SEQ ID NO 1
<211> LENGTH: 15
<212> TYPE: PRT
<213> ORGANISM: Artificial Sequence
<220> FEATURE:
<223> OTHER INFORMATION: Linker sequence
<220> FEATURE:
<221> NAME/KEY: REPEAT
<222> LOCATION: (1)..(3)
<223> OTHER INFORMATION: Portion of sequence repeated a times, wherein a
      is independently a number selected from 0, 1, 2, 3, 4, 5, 6, 7, 8,
      9, 10, 11, 12, 13, 14, 15, 16, 17, 18, 19, or 20
<220> FEATURE:
<221> NAME/KEY: MISC_FEATURE
<222> LOCATION: (1)..(15)
<223> OTHER INFORMATION: a + b + c + d + e are different from 0 and
      preferably are 2 or more, 3 or more, 4 or more or 5 or more
<220> FEATURE:
<221> NAME/KEY: REPEAT
<222> LOCATION: (4)..(6)
<223> OTHER INFORMATION: Portion of sequence repeated b times, wherein b
```

```
        is independently a number selected from 0, 1, 2, 3, 4, 5, 6, 7, 8,
        9, 10, 11, 12, 13, 14, 15, 16, 17, 18, 19, or 20
<220> FEATURE:
<221> NAME/KEY: REPEAT
<222> LOCATION: (7)..(9)
<223> OTHER INFORMATION: Portion of sequence repeated c times, wherein c
        is independently a number selected from 0, 1, 2, 3, 4, 5, 6, 7, 8,
        9, 10, 11, 12, 13, 14, 15, 16, 17, 18, 19, or 20
<220> FEATURE:
<221> NAME/KEY: REPEAT
<222> LOCATION: (10)..(12)
<223> OTHER INFORMATION: Portion of sequence repeated d times, wherein d
        is independently a number selected from 0, 1, 2, 3, 4, 5, 6, 7, 8,
        9, 10, 11, 12, 13, 14, 15, 16, 17, 18, 19, or 20
<220> FEATURE:
<221> NAME/KEY: REPEAT
<222> LOCATION: (13)..(15)
<223> OTHER INFORMATION: Portion of sequence repeated e times, wherein e
        is independently a number selected from 0, 1, 2, 3, 4, 5, 6, 7, 8,
        9, 10, 11, 12, 13, 14, 15, 16, 17, 18, 19, or 20

<400> SEQUENCE: 1

Gly Gly Ser Gly Ser Ser Gly Gly Gly Ser Ser Gly Gly Ser Gly
1               5                   10                  15

<210> SEQ ID NO 2
<211> LENGTH: 9
<212> TYPE: PRT
<213> ORGANISM: Artificial Sequence
<220> FEATURE:
<223> OTHER INFORMATION: Linker sequence

<400> SEQUENCE: 2

Gly Gly Ser Gly Gly Gly Gly Ser Gly
1               5
```

METHODS FOR PREDICTING THE USEFULNESS OF PROTEINS OR PROTEIN FRAGMENTS FOR IMMUNOTHERAPY

TECHNICAL FIELD OF THE INVENTION

The present invention relates to methods for predicting peptides or polypeptides such as T cell epitopes useful for immunotherapy such as for vaccination. In particular, the present invention relates to methods for predicting whether peptides or polypeptides such as tumor-associated antigens or epitopes, in particular tumor-associated neo-antigens or neo-epitopes, are immunogenic and, in particular, useful for immunotherapy such as for vaccination. The methods of the invention may be used, in particular, for the provision of vaccines which are specific for a patient's tumor and, thus, in the context of personalized cancer vaccines.

BACKGROUND OF THE INVENTION

The evolution of the immune system resulted in vertebrates in a highly effective network based on two types of defense: the innate and the adaptive immunity. In contrast to the evolutionary ancient innate immune system that relies on invariant receptors recognizing common molecular patterns associated with pathogens, the adaptive immunity is based on highly specific antigen receptors on B cells (B lymphocytes) and T cells (T lymphocytes) and clonal selection. While B cells raise humoral immune responses by secretion of antibodies, T cells mediate cellular immune responses leading to destruction of recognized cells.

T cells play a central role in cell-mediated immunity in humans and animals. The recognition and binding of a particular antigen is mediated by the T cell receptors expressed on the surface of T cells. The T cell receptor (TCR) of a T cell is able to interact with immunogenic peptides (epitopes) bound to major histocompatibility complex (MHC) molecules and presented on the surface of target cells. Specific binding of the TCR triggers a signal cascade inside the T cell leading to proliferation and differentiation into a maturated effector T cell. To be able to target a vast variety of antigens, the T cell receptors need to have a great diversity.

Antigen-specific immunotherapy aims to enhance or induce specific immune responses in patients to control infectious or malignant diseases. The identification of a growing number of pathogen- and tumor-associated antigens led to a broad collection of suitable targets for immunotherapy. Cells presenting immunogenic peptides (epitopes) derived from these antigens can be specifically targeted by either active or passive immunization strategies. Active immunization tends to induce and expand antigen-specific T cells in the patient, which are able to specifically recognize and kill diseased cells. In contrast passive immunization relies on the adoptive transfer of T cells, which were expanded and optional genetically engineered in vitro (adoptive T cell therapy; ACT).

Tumor vaccines aim to induce endogenous tumor specific immune responses by active immunization. Different antigen formats can be used for tumor vaccination including whole diseased cells, proteins, peptides or immunizing vectors such as RNA, DNA or viral vectors that can be applied either directly in vivo or in vitro by pulsing of DCs following transfer into the patient.

ACT based immunotherapy can be broadly defined as a form of passive immunization with previously sensitized T cells that are transferred to non-immune recipients or to the autologous host after ex vivo expansion from low precursor frequencies to clinically relevant cell numbers. An approach overcoming the limitations of ACT is the adoptive transfer of autologous T cells reprogrammed to express a tumor-reactive TCR of defined specificity during short-time ex vivo culture followed by reinfusion into the patient.

The discovery of multiple pathogen- and tumor-associated antigens has provided the basis for antigen-specific immunotherapy concepts. Tumor-associated antigens (TAA) are unusual proteins expressed on tumor cells due to their genetic instability, which have no or limited expression in normal cells. These TAAs can lead to specific recognition of malignant cells by the immune system.

Cancers may arise from the accumulation of genomic mutations and epigenetic changes, of which a fraction may have a causative role. In addition to tumor-associated antigens, human cancers carry on average 100-120 non-synonymous mutations, of which many are targetable by vaccines. More than 95% of mutations in a tumor are unique and patient specific. The number of protein changing somatic mutations, which may result in tumor specific T cell epitopes, is in the range of 30 to 400.

Mutations are regarded as ideal targets for cancer immunotherapy. As neo-epitopes with strict lack of expression in any healthy tissue, they are expected to be safe and could bypass the central tolerance mechanisms. We have recently proposed a personalized immunotherapy approach targeting the spectrum of individual mutations (Castle, J. C., et al., Cancer Res 72, 1081 (2012)).

In spite of the growing number of attractive target structures for immunotherapeutic approaches the definition of suitable epitopes for immunotherapy remains a challenge. Thus, there is a need for a model to predict whether an epitope, in particular a neo-epitope, will induce efficient immunity and, thus, will be useful in immunotherapy.

Here we show that immunogenic antigens and epitopes are strongly represented in certain subcellular compartments.

It is known that an immune response against tumor antigens, in particular mutated tumor antigens, is not effected by tumor cells themselves but rather antigen presenting cells, in particular dendritic cells, receiving tumor antigen released from tumor cells. It is also known that for achieving an effective immune response, released tumor antigen which is taken up by antigen presenting cells has to be processed and presented either by MHC class II for induction of a CD4 immune response (exogenous presentation) or by MHC class I for induction of a CD8 immune response (cross-presentation). For the latter immune response the existence of a CD4 immune response against the same or a different tumor antigen delivered to the same antigen presenting cell is required (Bennett et al., J. Exp. Med. 186, 65-70 (1997)).

Without wishing to be bound to a particular theory, it is believed that the cellular localization of an antigen in diseased cells such as tumor cells determines whether the antigen will be taken up and presented by antigen presenting cells. Exosomes released from diseased cells such as tumor cells contain mRNA, proteins as well as MHC peptide complexes and, thus can transfer these components to antigen presenting cells. Exosomes are produced by invagination and thus, contain besides endocytic membrane molecules mainly cytosolic components. Thus, it is believed that cytosolic components such as proteins are enriched in exosomes and can be transferred to antigen presenting cells. Exosomes can also productively transfer mRNA, which can be translated in the cells which take up the RNA. Thus, without wishing to be bound to a particular theory, it is believed that peptides or polypeptides which are included in exosomes, in particular cytosolic peptides or proteins, or peptides or polypeptides the coding RNA of which is included in exosomes according to the invention are particularly useful for immunotherapy because exosomes are taken up by antigen presenting cells and the peptides and proteins (optionally following translation of the coding RNA) are presented by the antigen presenting cells. The exosomes are thus transport vehicles for the peptides, proteins or RNA to antigen presenting cells and protect the peptides, proteins or RNA against degradation by proteases and ribonucleases. Alternatively, it is possible that peptides and proteins are taken up by antigen presenting cells as complexes with other molecules such as antibodies through a receptor dependent mechanism.

DESCRIPTION OF INVENTION

Summary of the Invention

In one aspect, the invention relates to a method for predicting the usefulness of a protein or a fragment thereof expressed by diseased cells for immunotherapy, the method comprising ascertaining the distribution or localization of the protein or a nucleic acid coding therefor, or of a fragment of the protein.

In one embodiment, the method comprises ascertaining whether the protein or a nucleic acid coding therefor, or a fragment of the protein is located or abundant in the cytosol and/or within exosomes in vivo.

In one embodiment, localization or abundance of the protein or a nucleic acid coding therefor, or of a fragment of the protein in the cytosol and/or within exosomes indicates that the protein or a fragment thereof is useful for immunotherapy.

In a further aspect, the invention relates to a method for predicting the usefulness of a protein or a fragment thereof expressed by diseased cells for immunotherapy, the method comprising ascertaining whether the protein or a fragment thereof is cross-presented by antigen presenting cells, preferably professional antigen presenting cells.

In one embodiment, cross-presentation of the protein or a fragment thereof by antigen presenting cells indicates that the protein or fragment thereof is useful for immunotherapy.

In one embodiment, ascertaining whether the protein or a fragment thereof is cross-presented by antigen presenting cells comprises ascertaining whether the protein or a nucleic acid coding therefor, or a fragment of the protein is located or abundant in the cytosol and/or within exosomes in vivo.

In one embodiment, localization or abundance of the protein or a nucleic acid coding therefor, or of a fragment of the protein in the cytosol and/or within exosomes indicates that the protein or a fragment thereof is cross-presented by antigen presenting cells.

In one embodiment, ascertaining whether the protein or a fragment thereof is cross-presented by antigen presenting cells comprises ascertaining an existing antibody response to the protein or a fragment thereof.

In one embodiment, an existing antibody response to the protein or a fragment thereof indicates that the protein or a fragment thereof is cross-presented by antigen presenting cells.

In one embodiment, ascertaining whether the protein or a fragment thereof is cross-presented by antigen presenting cells comprises ascertaining whether the protein or a fragment thereof binds to F actin.

In one embodiment, binding of the protein or a fragment thereof to F actin indicates that the protein or a fragment thereof is cross-presented by antigen presenting cells.

In one embodiment, ascertaining whether the protein or a fragment thereof is cross-presented by antigen presenting cells comprises ascertaining whether the protein or a fragment thereof binds to RNA.

In one embodiment, binding of the protein or a fragment thereof to RNA indicates that the protein or a fragment thereof is cross-presented by antigen presenting cells.

In one embodiment of all aspects of the invention, the protein fragment is present within exosomes as MHC peptide complex, preferably on the surface of exosomes.

In one embodiment of all aspects of the invention, localization or abundance of the protein or a nucleic acid coding therefor, or of a fragment of the protein in the cytosol indicates processing and presentation of the protein in the MHC I pathway, preferably of diseased cells. In one embodiment, processing and presentation of the protein in the MHC I pathway results in recognition of complexes formed by MHC I and fragments of the protein by CD8+ T cells.

In one embodiment of all aspects of the invention, localization or abundance of the protein or a nucleic acid coding therefor, or of a fragment of the protein within exosomes indicates accumulation of the protein or a nucleic acid coding therefor, or of a fragment of the protein in antigen presenting cells, preferably professional antigen presenting cells. In one embodiment, accumulation of the protein or a nucleic acid coding therefor, or of a fragment of the protein in antigen presenting cells indicates processing and presentation of the protein in the MHC I and/or MHC II pathway, preferably of the antigen presenting cells. In one embodiment, processing and presentation of the protein in the MHC I pathway results in recognition of complexes formed by MHC I and fragments of the protein by CD8+ T cells.

In a further aspect, the invention relates to a method for predicting the usefulness of a protein or a fragment thereof expressed by diseased cells for immunotherapy, the method comprising ascertaining one or more of the following:
  (a) ascertaining an existing antibody response to the protein or a fragment thereof,
  (b) ascertaining whether the protein or a fragment thereof binds to F actin, and/or
  (c) ascertaining whether the protein or a fragment thereof binds to RNA.

In one embodiment, an existing antibody response to the protein or a fragment thereof indicates that the protein or a fragment thereof is useful for immunotherapy.

In one embodiment, binding of the protein or a fragment thereof to F actin indicates that the protein or a fragment thereof is useful for immunotherapy.

In one embodiment, binding of the protein or a fragment thereof to RNA indicates that the protein or a fragment thereof is useful for immunotherapy.

In one embodiment of all aspects of the invention, the protein or a fragment thereof comprises a disease specific amino acid modification. In one embodiment, the amino acid modification is due to a disease specific somatic mutation.

In one embodiment of all aspects of the invention, the disease is cancer and the immunotherapy is anti-cancer immunotherapy.

In one embodiment of all aspects of the invention, the protein fragment is a MHC binding peptide or a potential MHC binding peptide.

In a further aspect, the invention relates to a method for selecting and/or ranking disease specific amino acid modifications for their usefulness in immunotherapy, the method comprising the steps of:
(i) identifying proteins expressed by diseased cells each protein comprising at least one disease specific amino acid modification, and
(ii) ascertaining the distribution or localization of a protein identified under (i) or a nucleic acid coding therefor, or of a fragment of the protein, and
(iii) repeating step (ii) for at least one further protein identified under (i).

In one embodiment, step (ii) comprises ascertaining whether the protein or a nucleic acid coding therefor, or a fragment of the protein is located or abundant in the cytosol and/or within exosomes in vivo.

In one embodiment, localization or abundance of the protein or a nucleic acid coding therefor, or of a fragment of the protein in the cytosol and/or within exosomes indicates that the disease specific amino acid modification is useful for immunotherapy.

In a further aspect, the invention relates to a method for selecting and/or ranking disease specific amino acid modifications for their usefulness in immunotherapy, the method comprising the steps of:
(i) identifying proteins expressed by diseased cells each protein comprising at least one disease specific amino acid modification, and
(ii) ascertaining whether a protein identified under (i) or a fragment of the protein is cross-presented by antigen presenting cells, preferably professional antigen presenting cells, and
(iii) repeating step (ii) for at least one further protein identified under (i).

In one embodiment, cross-presentation of the protein or a fragment thereof by antigen presenting cells indicates that the disease specific amino acid modification is useful for immunotherapy.

In a further aspect, the invention relates to a method for selecting and/or ranking disease specific amino acid modifications for their usefulness in immunotherapy, the method comprising the steps of:
(i) identifying proteins expressed by diseased cells each protein comprising at least one disease specific amino acid modification, and
(ii) ascertaining for a protein identified under (i) or a fragment of the protein one or more of the following:
(a) ascertaining an existing antibody response to the protein or a fragment thereof,
(b) ascertaining whether the protein or a fragment thereof binds to F actin, and/or
(c) ascertaining whether the protein or a fragment thereof binds to RNA, and
(iii) repeating step (ii) for at least one further protein identified under (i).

In one embodiment, an existing antibody response to the protein or a fragment thereof indicates that the disease specific amino acid modification is useful for immunotherapy.

In one embodiment, binding of the protein or a fragment thereof to F actin indicates that the disease specific amino acid modification is useful for immunotherapy.

In one embodiment, binding of the protein or a fragment thereof to RNA indicates that the disease specific amino acid modification is useful for immunotherapy.

In one embodiment of all aspects of the invention, the disease specific amino acid modification is comprised by a protein fragment which is a MHC binding peptide or a potential MHC binding peptide.

In one embodiment of all aspects of the invention, the method is used in the manufacture of a vaccine. In one embodiment, the vaccine is derived from one or more proteins or fragments thereof or one or more disease specific amino acid modifications which are predicted as being useful for immunotherapy.

In a further aspect, the invention relates to a method for providing a vaccine comprising the step: identifying one or more proteins or fragments thereof or one or more disease specific amino acid modifications which are predicted as being useful for immunotherapy by the method of any of the aspects described herein. In one embodiment, the method further comprises the step: providing a vaccine comprising a peptide or polypeptide comprising one or more proteins or fragments thereof or one or more disease specific amino acid modifications which are predicted as being useful for immunotherapy, or a nucleic acid encoding the peptide or polypeptide.

In a further aspect, the invention relates to a vaccine produced according to the method of any of the aspects described herein.

In one embodiment of all aspects of the invention, indication of a usefulness of a protein or a fragment thereof expressed by diseased cells for immunotherapy indicates that the protein or a fragment thereof upon administration (optionally in the format of the coding nucleic acid) will be immunogenic.

In one embodiment of all aspects of the invention, a protein fragment described herein is an MHC binding peptide or a potential MHC binding peptide (e.g. MHC binding prediction indicates that the protein fragment will bind to MHC). In one embodiment, the MHC binding peptide is a modified peptide which is a fragment of a modified protein.

In one embodiment, amino acid modifications in proteins or peptides are identified by identifying non-synonymous mutations in one or more protein-coding regions.

In one embodiment, amino acid modifications are identified by partially or completely sequencing the genome or transcriptome of one or more cells such as one or more cancer cells and optionally one or more non-cancerous cells and identifying mutations in one or more protein-coding regions. In one embodiment, said mutations are somatic mutations. In one embodiment, said mutations are cancer mutations.

In one embodiment, in particular in order to provide a personalized vaccine for a patient such as a cancer patient, the modification(s) are present in said patient and the methods of the invention are performed for said patient. In a further aspect, the present invention provides a vaccine which is obtainable using the methods according to the invention. Preferred embodiments of such vaccines are described herein.

A vaccine provided according to the invention may comprise a pharmaceutically acceptable carrier and may optionally comprise one or more adjuvants, stabilizers etc. The vaccine may in the form of a therapeutic or prophylactic vaccine.

Another aspect relates to a method for inducing an immune response in a patient, comprising administering to the patient a vaccine provided according to the invention.

Another aspect relates to a method of treating a patient comprising the steps:
(a) providing an immunotherapeutic agent described herein such as a vaccine using the methods according to the invention; and (b) administering said immunotherapeutic agent to the patient.

Another aspect relates to a method of treating a patient comprising administering an immunotherapeutic agent described herein such as a vaccine to the patient.

In one embodiment, the patient is a cancer patient and the vaccine is an anti-cancer vaccine such as a vaccine the administration of which provides cancer specific neo-epitopes.

In further aspects, the invention provides the vaccines described herein for use in the methods of treatment described herein, in particular for use in treating or preventing cancer.

The treatments of cancer described herein can be combined with surgical resection and/or radiation and/or traditional chemotherapy.

Other features and advantages of the instant invention will be apparent from the following detailed description and claims.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., (1995) *Helvetica Chimica Acta,* CH-4010 Basel, Switzerland.

The practice of the present invention will employ, unless otherwise indicated, conventional methods of biochemistry, cell biology, immunology, and recombinant DNA techniques which are explained in the literature in the field (cf., e.g., *Molecular Cloning: A Laboratory Manual, 2$^{nd}$ Edition,* J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention The present invention envisions the immunotherapy of diseases, in particular cancer diseases by utilizing a protein or a protein fragment present in diseased cells as a label for and targeting diseased cells. In particular, the diseased cells may be targeted by targeting a fragment of a protein presented on the surface of the diseased cells in the context of MHC. The immunotherapy according to the present invention is to be effected by means of active and/or passive immunotherapeutic approaches.

Specifically, the present invention aims at defining suitable proteins or fragments thereof for immunotherapy. Once a suitable protein has been identified this protein or a fragment thereof (optionally as part of a larger polypeptide) or a nucleic acid coding for the protein or fragment (optionally as part of a larger polypeptide) may be used as a vaccine in order to enhance or induce an immune response against the protein or a fragment thereof, in particular by inducing and/or activating appropriate effector cells such as T cells that recognize the protein or a fragment thereof (in particular when presented in the context of MHC) through an appropriate receptor (such as T cell receptor or artificial T cell receptor). Alternatively or additionally, effector cells such as T cells that recognize the protein or a fragment thereof (in particular when presented in the context of MHC) through an appropriate receptor (such as T cell receptor or artificial T cell receptor) may be administered. Without wishing to be bound to a particular theory, it is believed that the protein or a fragment thereof which is predicted as being useful in immunotherapy by the present invention has a high likelihood of being taken up by antigen presenting cells and being presented by the antigen presenting cells, in particular by cross-presentation, thus ultimately resulting in an efficient immune response against diseased cells expressing the protein or a fragment thereof.

The proteins defined according to the invention as being useful or suitable for immunotherapy are also termed "antigens" herein. The proteins fragments defined according to the invention as being useful or suitable for immunotherapy are also termed "epitopes" herein.

The immunotherapeutic approaches according to the invention include immunization with: i) protein or peptide (native or modified), ii) nucleic acid encoding protein or peptide, iii) recombinant cells encoding protein or peptide, iv) recombinant viruses encoding protein or peptide and v) antigen presenting cells pulsed with protein or peptide (native or modified) or transfected with nucleic acids encoding protein or peptide.

The immunotherapeutic approaches according to the invention also include transfer of: vi) T cell receptors that recognize protein or peptide, and vii) effector cells (such as T cells) encoding receptors that recognize protein or peptide, in particular when presented in the context of MHC.

Preferred proteins and fragments according to the invention are expressed in a disease specific manner, e.g. they are disease-associated antigens or epitopes, (e.g. the presence of a protein or cells expressing a protein is characteristic for the disease) and/or comprise one or more disease specific amino acid modifications, e.g. they are disease-associated neo-antigens or neo-epitopes.

Preferably, a disease specific amino acid modification is due to one or more disease specific somatic mutations. In one particularly preferred embodiment, a disease specific amino acid modification is a cancer specific amino acid modification and a disease specific somatic mutation is a cancer specific somatic mutation. Thus, according to the invention, a vaccine preferably features disease specific amino acid modifications/disease specific somatic mutations of a patient and preferably upon administration provides one or more mutation based neo-epitopes. Thus, the vaccine may comprise a peptide or polypeptide comprising one or more mutation based neo-epitopes, or a nucleic acid encoding said peptide or polypeptide. In one embodiment, disease specific amino acid modifications are identified by identifying disease specific somatic mutations, e.g. by sequencing genomic DNA and/or RNA of diseased tissue or one or more diseased cells.

According to the invention the step of identifying disease specific amino acid modifications and/or identifying disease specific somatic mutations may be performed prior to or after the methods of the invention of predicting the usefulness of a protein or a fragment thereof expressed by diseased cells for immunotherapy. In one preferred embodiment of the invention, disease specific amino acid modifications and/or disease specific somatic mutations are determined first in a diseased specimen of a patient and this is followed by a prediction of the usefulness of the protein comprising one or more disease specific amino acid modifications or of a fragment thereof comprising one or more disease specific amino acid modifications for immunotherapy according to the methods of the invention. Once identified, disease specific amino acid modifications (respectively proteins comprising one or more disease specific amino acid modifications or fragments thereof comprising one or more disease specific amino acid modifications) may also be selected and/or ranked for their usefulness in immunotherapy according to methods of the invention.

The term "exosomes" relates to cell-derived vesicles that are present in biological fluids, including blood, urine, and cultured medium of cell cultures. Exosomes are either released from the cell when multivesicular bodies fuse with the plasma membrane or they are released directly from the plasma membrane. Exosomes contain various molecular constituents of their cell of origin, including proteins and RNA. Although the exosomal protein composition varies with the cell and tissue of origin, most exosomes contain an evolutionarily-conserved common set of protein molecules. Exosomes can transfer molecules from one cell to another via membrane vesicle trafficking, thereby influencing the immune system, such as dendritic cells and B cells, and may play a functional role in mediating adaptive immune responses to pathogens and tumors.

As used herein, the term "cytosol" refers to the portion of the cytoplasm not within membrane-bound sub-structures of the cell.

According to the present invention, the term "peptide" refers to substances comprising two or more, preferably 3 or more, preferably 4 or more, preferably 6 or more, preferably 8 or more, preferably 10 or more, preferably 13 or more, preferably 16 more, preferably 21 or more and up to preferably 8, 10, 20, 30, 40 or 50, in particular 100 amino acids joined covalently by peptide bonds. The term "polypeptide" or "protein" refers to large peptides, preferably to peptides with more than 100 amino acid residues, but in general the terms "peptide", "polypeptide" and "protein" are synonyms and are used interchangeably herein.

According to the invention, the term "modification" with respect to peptides, polypeptides or proteins relates to a sequence change in a peptide, polypeptide or protein compared to a parental sequence such as the sequence of a wildtype peptide, polypeptide or protein. The term includes amino acid insertion variants, amino acid addition variants, amino acid deletion variants and amino acid substitution variants, preferably amino acid substitution variants. All these sequence changes according to the invention may potentially create new epitopes.

Amino acid insertion variants comprise insertions of single or two or more amino acids in a particular amino acid sequence.

Amino acid addition variants comprise amino- and/or carboxy-terminal fusions of one or more amino acids, such as 1, 2, 3, 4 or 5, or more amino acids.

Amino acid deletion variants are characterized by the removal of one or more amino acids from the sequence, such as by removal of 1, 2, 3, 4 or 5, or more amino acids.

Amino acid substitution variants are characterized by at least one residue in the sequence being removed and another residue being inserted in its place.

According to the invention, a modification or modified peptide may be derived from a protein comprising a modification.

The term "derived" means according to the invention that a particular entity, in particular a particular peptide sequence, is present in the object from which it is derived. In the case of amino acid sequences, especially particular sequence regions, "derived" in particular means that the relevant amino acid sequence is derived from an amino acid sequence in which it is present.

According to the invention, proteins described herein preferably comprise one or more disease specific amino acid modifications. In one embodiment, these one or more disease specific amino acid modifications are located within epitopes or potential epitopes of the protein. Thus, preferred proteins described herein are neo-antigens preferably comprising one or more neo-epitopes. Similarly, a preferred protein fragment described herein is a fragment of a protein comprising one or more disease specific amino acid modifications, wherein preferably one or more disease specific amino acid modifications are located within the fragment of the protein. Thus, a preferred protein fragment described herein is a neo-epitope.

According to the invention, the term "neo-antigen" relates to a peptide or protein including one or more amino acid modifications compared to the parental peptide or protein. For example, the neo-antigen may be a tumor-associated neo-antigen, wherein the term "tumor-associated neo-antigen" includes a peptide or protein including amino acid modifications due to tumor specific mutations.

According to the invention, the term "disease specific mutation" relates to a somatic mutation that is present in the nucleic acid of a diseased cell but absent in the nucleic acid of a corresponding normal, i.e. non-diseased, cell.

According to the invention, the term "tumor specific mutation" or "cancer specific mutation" relates to a somatic mutation that is present in the nucleic acid of a tumor or cancer cell but absent in the nucleic acid of a corresponding normal, i.e. non-tumorous or non-cancerous, cell. The terms "tumor specific mutation" and "tumor mutation" and the terms "cancer specific mutation" and "cancer mutation" are used interchangeably herein.

The term "immune response" relates to a reaction of the immune system such as to immunogenic organisms, such as bacteria or viruses, cells or substances. The term "immune response" includes the innate immune response and the adaptive immune response. Preferably, the immune response is related to an activation of immune cells, an induction of cytokine biosynthesis and/or antibody production.

It is preferred that the immune response induced by the compositions described herein comprises the steps of activation of antigen presenting cells, such as dendritic cells and/or macrophages, presentation of an antigen or fragment thereof by said antigen presenting cells and activation of cytotoxic T cells due to this presentation.

"Inducing an immune response" may mean that there was no immune response before induction, but it may also mean that there was a certain level of immune response before induction and after induction said immune response is enhanced. Thus, "inducing an immune response" also includes "enhancing an immune response". Preferably, after inducing an immune response in a subject, said subject is protected from developing a disease such as a cancer disease or the disease condition is ameliorated by inducing an immune response. For example, an immune response against a tumor-expressed antigen may be induced in a patient having a cancer disease or in a subject being at risk of developing a cancer disease. Inducing an immune response in this case may mean that the disease condition of the subject is ameliorated, that the subject does not develop metastases, or that the subject being at risk of developing a cancer disease does not develop a cancer disease.

The terms "cellular immune response" and "cellular response" or similar terms refer to an immune response directed to cells characterized by presentation of an antigen with class I or class II MHC involving T cells or T-lymphocytes which act as either "helpers" or "killers". The helper T cells (also termed $CD4^+$ T cells) play a central role by regulating the immune response and the killer cells (also termed cytotoxic T cells, cytolytic T cells, $CD8^+$ T cells or CTLs) kill diseased cells such as cancer cells, preventing the production of more diseased cells. In preferred embodiments, the present invention involves the stimulation of an anti-disease CTL response against diseased cells expressing one or more disease-associated antigens and preferably presenting such disease-associated antigens with class I MHC, particularly an anti-tumor CTL response against tumor cells expressing one or more tumor-expressed antigens and preferably presenting such tumor-expressed antigens with class I MHC.

According to the invention, the term "antigen" or "immunogen" covers any substance, preferably a peptide or protein, that is a target of an immune response and/or that will elicit an immune response. In particular, an "antigen" relates to any substance that reacts specifically with antibodies or T-lymphocytes (T-cells). According to the present invention, the term "antigen" comprises any molecule which comprises at least one epitope such as a T cell epitope. Preferably, an antigen in the context of the present invention is a molecule which, optionally after processing, induces an immune reaction, which is preferably specific for the antigen or cells expressing the antigen. According to the present invention, any suitable antigen may be used, which is a candidate for an immune reaction, wherein the immune reaction is preferably a cellular immune reaction. In the context of the embodiments of the present invention, the antigen is preferably presented by a cell, preferably by an antigen presenting cell, in the context of MHC molecules, which results in an immune reaction against the antigen. An antigen is preferably a product which corresponds to or is derived from a naturally occurring antigen. Such naturally occurring antigens may include or may be derived from allergens, viruses, bacteria, fungi, parasites and other infectious agents and pathogens or an antigen may also be a tumor antigen. According to the present invention, an antigen may correspond to a naturally occurring product, for example, a viral protein, or a part thereof. In preferred embodiments, the antigen is a surface polypeptide, i.e. a polypeptide naturally displayed on the surface of a cell, a pathogen, a bacterium, a virus, a fungus, a parasite, an allergen, or a tumor. The antigen may elicit an immune response against a cell, a pathogen, a bacterium, a virus, a fungus, a parasite, an allergen, or a tumor.

The term "disease-associated antigen" is used in it broadest sense to refer to any antigen associated with a disease. A disease-associated antigen is a molecule which contains epitopes that will stimulate a host's immune system to make a cellular antigen-specific immune response and/or a humoral antibody response against the disease. The disease-associated antigen may therefore be used for therapeutic purposes. Disease-associated antigens are preferably associated with infection by microbes, typically microbial antigens, or associated with cancer, typically tumors.

The term "pathogen" refers to pathogenic biological material capable of causing disease in an organism, preferably a vertebrate organism. Pathogens include microorganisms such as bacteria, unicellular eukaryotic organisms (protozoa), fungi, as well as viruses.

The terms "epitope", "antigen peptide", "antigen epitope", "immunogenic peptide" and "MHC binding peptide" are used interchangeably herein and refer to an antigenic determinant in a molecule such as an antigen, i.e., to a part in or fragment of an immunologically active compound that is recognized by the immune system, for example, that is recognized by a T cell, in particular when presented in the context of MHC molecules. An epitope of a protein preferably comprises a continuous or discontinuous portion of said protein and is preferably between 5 and 100, preferably between 5 and 50, more preferably between 8 and 30, most preferably between 10 and 25 amino acids in length, for example, the epitope may be preferably 9, 10, 11, 12, 13, 14, 15, 16, 17, 18, 19, 20, 21, 22, 23, 24, or 25 amino acids in length. According to the invention an epitope may bind to MHC molecules such as MHC molecules on the surface of a cell and thus, may be a "MHC binding peptide" or "antigen peptide".

The term "major histocompatibility complex" and the abbreviation "MHC" include MHC class I and MHC class II molecules and relate to a complex of genes which is present in all vertebrates. MHC proteins or molecules are important for signaling between lymphocytes and antigen presenting cells or diseased cells in immune reactions, wherein the MHC proteins or molecules bind peptides and present them for recognition by T cell receptors. The proteins encoded by the MHC are expressed on the surface of cells, and display both self-antigens (peptide fragments from the cell itself) and non-self-antigens (e.g., fragments of invading microorganisms) to a T cell. Preferred such immunogenic portions bind to an MHC class I or class II molecule. As used herein, an immunogenic portion is said to "bind to" an MHC class I or class II molecule if such binding is detectable using any assay known in the art. The term "MHC binding peptide" relates to a peptide which binds to an MHC class I and/or an MHC class II molecule. In the case of class I MHC/peptide complexes, the binding peptides are typically 8-10 amino acids long although longer or shorter peptides may be effective. In the case of class II MHC/peptide complexes, the binding peptides are typically 10-25 amino acids long and are in particular 13-18 amino acids long, whereas longer and shorter peptides may be effective. In one preferred embodiment of all aspects of the invention an MHC molecule is an HLA molecule.

If a peptide is part of a larger entity comprising additional sequences, e.g. of a vaccine sequence or polypeptide, and is to be presented following processing, in particular following cleavage, the peptide produced by processing has a length which is suitable for binding to an MHC molecule, in particular a class I MHC molecule, and preferably is 7-30 amino acids in length such as 7-20 amino acids in length, more preferably 7-12 amino acids in length, more preferably 8-11 amino acids in length, in particular 9 or 10 amino acids in length. Preferably, the sequence of the peptide which is to be presented following processing is derived from the amino acid sequence of an antigen or polypeptide used for vaccination, i.e., its sequence substantially corresponds and is preferably completely identical to a fragment of the antigen or polypeptide.

Thus, an MHC binding peptide in one embodiment comprises a sequence which substantially corresponds and is preferably completely identical to a fragment of an antigen.

As used herein the term "neo-epitope" refers to an epitope that is not present in a reference such as a normal non-diseased (e.g. non-cancerous) or germline cell but is found in diseased cells (e.g. cancer cells). This includes, in particular, situations wherein in a normal non-diseased or germline cell a corresponding epitope is found, however, due to one or more mutations in a diseased cell the sequence of the epitope is changed so as to result in the neo-epitope.

As used herein, the term "T cell epitope" refers to a peptide which binds to a MHC molecule in a configuration recognized by a T cell receptor. Typically, T cell epitopes are presented on the surface of an antigen-presenting cell.

A T cell epitope according to the invention preferably relates to a portion or fragment of an antigen which is capable of stimulating an immune response, preferably a cellular response against the antigen or cells characterized by expression of the antigen and preferably by presentation of the antigen such as diseased cells, in particular cancer cells. Preferably, a T cell epitope is capable of stimulating a cellular response against a cell characterized by presentation of an antigen with class I MHC and preferably is capable of stimulating an antigen-responsive cytotoxic T-lymphocyte (CTL).

In one embodiment, a vaccine according to the present invention comprises an epitope suitable for vaccination of a target organism. A person skilled in the art will know that one of the principles of immunobiology and vaccination is based on the fact that an immunoprotective reaction to a disease is produced by immunizing an organism with a vaccine, which is immunologically relevant with respect to the disease to be treated. According to the present invention, an antigen is selected from the group comprising a self-antigen and non-self-antigen. A non-self-antigen is preferably a bacterial antigen, a virus antigen, a fungus antigen, an allergen or a parasite antigen. It is preferred that the antigen comprises an epitope that is capable of eliciting an immune response in a target organism. For example, the epitope may elicit an immune response against a bacterium, a virus, a fungus, a parasite, an allergen, or a tumor.

In some embodiments the non-self-antigen is a bacterial antigen. In some embodiments, the antigen elicits an immune response against a bacterium which infects animals, including birds, fish and mammals, including domesticated animals. Preferably, the bacterium against which the immune response is elicited is a pathogenic bacterium.

In some embodiments the non-self-antigen is a virus antigen. A virus antigen may for example be a peptide from a virus surface protein, e.g. a capsid polypeptide or a spike polypeptide. In some embodiments, the antigen elicits an immune response against a virus which infects animals, including birds, fish and mammals, including domesticated animals. Preferably, the virus against which the immune response is elicited is a pathogenic virus.

In some embodiments the non-self-antigen is a polypeptide or a protein from a fungus. In some embodiments, the antigen elicits an immune response against a fungus which infects animals, including birds, fish and mammals, including domesticated animals. Preferably, the fungus against which the immune response is elicited is a pathogenic fungus.

In some embodiments the non-self-antigen is a polypeptide or protein from a unicellular eukaryotic parasite. In some embodiments, the antigen elicits an immune response against a unicellular eukaryotic parasite, preferably a pathogenic unicellular eukaryotic parasite. Pathogenic unicellular eukaryotic parasites may be e.g. from the genus *Plasmodium*, e.g. *P. falciparum*, *P. vivax*, *P. malariae* or *P. ovale*, from the genus *Leishmania*, or from the genus *Trypanosoma*, e.g. *T. cruzi* or *T. brucei*.

In some embodiments the non-self-antigen is an allergenic polypeptide or an allergenic protein. An allergenic protein or allergenic polypeptide is suitable for allergen immunotherapy, also known as hypo-sensitization.

In some embodiments the antigen is a self-antigen, particularly a tumor antigen. Tumor antigens and their determination are known to the skilled person.

In the context of the present invention, the term "tumor antigen" or "tumor-associated antigen" relates to proteins that are under normal conditions specifically expressed in a limited number of tissues and/or organs or in specific developmental stages, for example, the tumor antigen may be under normal conditions specifically expressed in stomach tissue, preferably in the gastric mucosa, in reproductive organs, e.g., in testis, in trophoblastic tissue, e.g., in placenta, or in germ line cells, and are expressed or aberrantly expressed in one or more tumor or cancer tissues. In this context, "a limited number" preferably means not more than 3, more preferably not more than 2. The tumor antigens in the context of the present invention include, for example, differentiation antigens, preferably cell type specific differentiation antigens, i.e., proteins that are under normal conditions specifically expressed in a certain cell type at a certain differentiation stage, cancer/testis antigens, i.e., proteins that are under normal conditions specifically expressed in testis and sometimes in placenta, and germ line specific antigens. In the context of the present invention, the tumor antigen is preferably associated with the cell surface of a cancer cell and is preferably not or only rarely expressed in normal tissues. Preferably, the tumor antigen or the aberrant expression of the tumor antigen identifies cancer cells. In the context of the present invention, the tumor antigen that is expressed by a cancer cell in a subject, e.g., a patient suffering from a cancer disease, is preferably a self-protein in said subject. In preferred embodiments, the tumor antigen in the context of the present invention is expressed under normal conditions specifically in a tissue or organ that is non-essential, i.e., tissues or organs which when damaged by the immune system do not lead to death of the subject, or in organs or structures of the body which are not or only hardly accessible by the immune system. Preferably, the amino acid sequence of the tumor antigen is identical between the tumor antigen which is expressed in normal tissues and the tumor antigen which is expressed in cancer tissues.

Examples for tumor antigens that may be useful in the present invention are p53, ART-4, BAGE, beta-catenin/m, Bcr-abL CAMEL, CAP-1, CASP-8, CDC27/m, CDK4/m, CEA, the cell surface proteins of the claudin family, such as CLAUDIN-6, CLAUDIN-18.2 and CLAUDIN-12, c-MYC, CT, Cyp-B, DAM, ELF2M, ETV6-AML1, G250, GAGE, GnT-V, Gap100, HAGE, HER-2/neu, HPV-E7, HPV-E6, HAST-2, hTERT (or hTRT), LAGE, LDLR/FUT, MAGE-A, preferably MAGE-A1, MAGE-A2, MAGE-A3, MAGE-A4, MAGE-A5, MAGE-A6, MAGE-A7, MAGE-A8, MAGE-A9, MAGE-A10, MAGE-A11, or MAGE-A12, MAGE-B, MAGE-C, MART-1/Melan-A, MC1R, Myosin/m, MUC1, MUM-1, -2, -3, NA88-A, NF1, NY-ESO-1, NY-BR-1, p190 minor BCR-abL, Pm1/RARa, PRAME, proteinase 3, PSA, PSM, RAGE, RU1 or RU2, SAGE, SART-1 or SART-3, SCGB3A2, SCP1, SCP2, SCP3, SSX, SURVIVIN, TEL/AML1, TPI/m, TRP-1, TRP-2, TRP-2/INT2, TPTE and WT. Particularly preferred tumor antigens include CLAUDIN-18.2 (CLDN18.2) and CLAUDIN-6 (CLDN6).

The term "immunogenicity" relates to the relative effectivity to induce an immune response that is preferably associated with therapeutic treatments, such as treatments against cancers. As used herein, the term "immunogenic" relates to the property of having immunogenicity. For example, the term "immunogenic modification" when used in the context of a peptide, polypeptide or protein relates to the effectivity of said peptide, polypeptide or protein to induce an immune response that is caused by and/or directed against said modification. Preferably, the non-modified peptide, polypeptide or protein does not induce an immune response, induces a different immune response or induces a different level, preferably a lower level, of immune response.

According to the invention, the term "immunogenicity" or "immunogenic" preferably relates to the relative effectivity to induce a biologically relevant immune response, in particular an immune response which is useful for vaccination. Thus, in one preferred embodiment, an amino acid modification or modified peptide is immunogenic if it induces an immune response against the target modification in a subject, which immune response may be beneficial for therapeutic or prophylactic purposes.

As used herein, the term "predicting the usefulness of a protein or a fragment thereof for immunotherapy" refers to a prediction whether the protein or one or more fragments thereof such as epitopes, in particular T cell epitopes, will be useful for inducing an immune response or targeting an immune response. If a protein such as a disease-associated antigen is predicted as being useful for immunotherapy, for example, epitopes of said protein may be used for vaccination as described herein or effector cells targeting an epitope of said protein may be administered. Preferably, a protein the usefulness of which for immunotherapy is to be predicted according to the invention is expressed in diseased cells of a patient.

According to the invention, a T cell epitope may be present in a vaccine as a part of a larger entity such as a vaccine sequence and/or a polypeptide comprising more than one T cell epitope. The presented peptide or T cell epitope is produced following suitable processing. Also, T cell epitopes may be modified at one or more residues that are not essential for TCR recognition or for binding to MHC. Such modified T cell epitopes may be considered immunologically equivalent. Preferably a T cell epitope when presented by MHC and recognized by a T cell receptor is able to induce in the presence of appropriate co-stimulatory signals, clonal expansion of the T cell carrying the T cell receptor specifically recognizing the peptide/MHC-complex. Preferably, a T cell epitope comprises an amino acid sequence substantially corresponding to the amino acid sequence of a fragment of an antigen. Preferably, said fragment of an antigen is an MHC class I and/or class II presented peptide.

"Antigen processing" or "processing" refers to the degradation of a peptide, polypeptide or protein into procession products, which are fragments of said peptide, polypeptide or protein (e.g., the degradation of a polypeptide into peptides) and the association of one or more of these fragments (e.g., via binding) with MHC molecules for presentation by cells, preferably antigen presenting cells, to specific T cells.

Class II-restricted antigens are largely derived from exogenous proteins that enter antigen presenting cells via the endocytic pathway and are processed in the endosomal compartment. By contrast, antigens recognized by class I-restricted effector CTL are usually derived from endogenously synthesized proteins. Thus, exogenous proteins cannot provide antigenic determinants for class I-restricted effector CTL unless they are introduced directly into the cytoplasm of target cells.

The term "cross-presentation" relates to the ability of antigen-presenting cells to take up, process and present extracellular antigens with MHC class I molecules to CD8 T cells (cytotoxic T cells). Cross-priming describes the stimulation of naive cytotoxic CD8+ T cells by this process. Antigen-presenting cells capable of cross-presentation are primarily dendritic cells, but macrophages, B lymphocytes and sinusoidal endothelial cells have also been shown to be able to do so.

Cross-priming has been shown to occur for viral proteins and tumor antigens. This has led to the proposal that cross-priming may provide the immune system with a mechanism by which it can detect and respond to tissue-tropic viruses that do not infect professional APC. In the absence of such a mechanism, viruses could escape immunosurveillance by avoiding professional APC. This mechanism also provides the immune system with a means to survey neo-antigens expressed by newly arising tumor cells. Like exogenous foreign antigens, exogenous self antigens can enter the class I-presentation pathway.

"Antigen presenting cells" (APC) are cells which present peptide fragments of protein antigens in association with MHC molecules on their cell surface. Some APCs may activate antigen specific T cells.

Professional antigen-presenting cells are very efficient at internalizing antigen, either by phagocytosis or by receptor-mediated endocytosis, and then displaying a fragment of the antigen, bound to a class II MHC molecule, on their membrane. The T cell recognizes and interacts with the antigen-class II MHC molecule complex on the membrane of the antigen-presenting cell. An additional co-stimulatory signal is then produced by the antigen-presenting cell, leading to activation of the T cell. The expression of co-stimulatory molecules is a defining feature of professional antigen-presenting cells.

The main types of professional antigen-presenting cells are dendritic cells, which have the broadest range of antigen presentation, and are probably the most important antigen-presenting cells, macrophages, B-cells, and certain activated epithelial cells. Dendritic cells (DCs) are leukocyte populations that present antigens captured in peripheral tissues to T cells via both MHC class II and I antigen presentation pathways. It is well known that dendritic cells are potent inducers of immune responses and the activation of these cells is a critical step for the induction of antitumoral immunity. Dendritic cells are conveniently categorized as "immature" and "mature" cells, which can be used as a simple way to discriminate between two well characterized phenotypes. However, this nomenclature should not be construed to exclude all possible intermediate stages of differentiation. Immature dendritic cells are characterized as antigen presenting cells with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e. g. CD54 and CD11) and costimulatory molecules (e. g., CD40, CD80, CD86 and 4-1 BB). Dendritic cell maturation is referred to as the status of dendritic cell activation at which such antigen-presenting dendritic cells lead to T cell priming, while presentation by immature dendritic cells results in tolerance. Dendritic cell maturation is chiefly caused by biomolecules with microbial features detected by innate receptors (bacterial DNA, viral RNA, endotoxin, etc.), pro-inflammatory cytokines (TNF, IL-1, IFNs), ligation of CD40 on the dendritic cell surface by CD40L, and substances released from cells undergoing stressful cell death. The dendritic cells can be derived by culturing bone marrow cells in vitro with cytokines, such as granulocyte-macrophage colony-stimulating factor (GM-CSF) and tumor necrosis factor alpha.

Non-professional antigen-presenting cells do not constitutively express the MHC class II proteins required for interaction with naive T cells; these are expressed only upon stimulation of the non-professional antigen-presenting cells by certain cytokines such as IFNγ.

By "cell characterized by presentation of an antigen" or "cell presenting an antigen" or similar expressions is meant a cell such as a diseased cell, e.g. a cancer cell, or an antigen presenting cell presenting an antigen or a fragment derived from said antigen, e.g. by processing of the antigen, in the context of MHC molecules, in particular MHC Class I molecules. Similarly, the terms "disease characterized by presentation of an antigen" denotes a disease involving cells characterized by presentation of an antigen, in particular with class I MHC. Presentation of an antigen by a cell may be effected by transfecting the cell with a nucleic acid such as RNA encoding the antigen.

By "fragment of an antigen which is presented" or similar expressions is meant that the fragment can be presented by MHC class I or class II, preferably MHC class I, e.g. when added directly to antigen presenting cells. In one embodiment, the fragment is a fragment which is naturally presented by cells expressing an antigen.

"Target cell" shall mean a cell which is a target for an immune response such as a cellular immune response. Target cells include cells that present an antigen, i.e. a peptide fragment derived from an antigen, and include any undesirable cell such as a cancer cell. In preferred embodiments, the target cell is a cell expressing an antigen as described herein and preferably presenting said antigen with class I MHC.

The term "portion" refers to a fraction. With respect to a particular structure such as an amino acid sequence or protein the term "portion" thereof may designate a continuous or a discontinuous fraction of said structure. Preferably, a portion of an amino acid sequence comprises at least 1%, at least 5%, at least 10%, at least 20%, at least 30%, preferably at least 40%, preferably at least 50%, more preferably at least 60%, more preferably at least 70%, even more preferably at least 80%, and most preferably at least 90% of the amino acids of said amino acid sequence. Preferably, if the portion is a discontinuous fraction said discontinuous fraction is composed of 2, 3, 4, 5, 6, 7, 8, or more parts of a structure, each part being a continuous element of the structure. For example, a discontinuous fraction of an amino acid sequence may be composed of 2, 3, 4, 5, 6, 7, 8, or more, preferably not more than 4 parts of said amino acid sequence, wherein each part preferably comprises at least 5 continuous amino acids, at least 10 continuous amino acids, preferably at least 20 continuous amino acids, preferably at least 30 continuous amino acids of the amino acid sequence.

The terms "part" and "fragment" are used interchangeably herein and refer to a continuous element. For example, a part of a structure such as an amino acid sequence or protein refers to a continuous element of said structure. A portion, a part or a fragment of a structure preferably comprises one or more functional properties of said structure. For example, a portion, a part or a fragment of an epitope, peptide or protein is preferably immunologically equivalent to the epitope, peptide or protein it is derived from. In the context of the present invention, a "part" of a structure such as an amino acid sequence preferably comprises, preferably consists of at least 10%, at least 20%, at least 30%, at least 40%, at least 50%, at least 60%, at least 70%, at least 80%, at least 85%, at least 90%, at least 92%, at least 94%, at least 96%, at least 98%, at least 99% of the entire structure or amino acid sequence.

The term "effector cell", "immune effector cell" or "immunoreactive cell" in the context of the present invention relates to a cell which exerts effector functions during an immune reaction. An "immunoreactive cell" preferably is capable of binding an antigen or a cell characterized by presentation of an antigen or a peptide fragment thereof (e.g. a T cell epitope) and mediating an immune response. For example, such cells secrete cytokines and/or chemokines, secrete antibodies, recognize cancerous cells, and optionally eliminate such cells. For example, immunoreactive cells comprise T cells (cytotoxic T cells, helper T cells, tumor infiltrating T cells), B cells, natural killer cells, neutrophils, macrophages, and dendritic cells. Preferably, in the context of the present invention, immunoreactive cells are T cells, preferably CD4+ and/or CD8+ T cells.

Preferably, an "immunoreactive cell" recognizes an antigen or a peptide fragment thereof with some degree of specificity, in particular if presented in the context of MHC molecules such as on the surface of antigen presenting cells or diseased cells such as cancer cells. Preferably, said recognition enables the cell that recognizes an antigen or a peptide fragment thereof to be responsive or reactive. If the cell is a helper T cell (CD4+ T cell) bearing receptors that recognize an antigen or a peptide fragment thereof in the context of MHC class II molecules such responsiveness or reactivity may involve the release of cytokines and/or the activation of CD8+ lymphocytes (CTLs) and/or B-cells. If the cell is a CTL such responsiveness or reactivity may involve the elimination of cells presented in the context of MHC class I molecules, i.e., cells characterized by presentation of an antigen with class I MHC, for example, via apoptosis or perforin-mediated cell lysis. According to the invention, CTL responsiveness may include sustained calcium flux, cell division, production of cytokines such as IFN-γ and TNF-α, upregulation of activation markers such as CD44 and CD69, and specific cytolytic killing of antigen expressing target cells. CTL responsiveness may also be determined using an artificial reporter that accurately indicates CTL responsiveness. Such CTL that recognize an antigen or an antigen fragment and are responsive or reactive are also termed "antigen-responsive CTL" herein. If the cell is a B cell such responsiveness may involve the release of immunoglobulins.

The terms "T cell" and "T lymphocyte" are used interchangeably herein and include T helper cells (CD4+ T cells) and cytotoxic T cells (CTLs, CD8+ T cells) which comprise cytolytic T cells.

T cells belong to a group of white blood cells known as lymphocytes, and play a central role in cell-mediated immunity. They can be distinguished from other lymphocyte types, such as B cells and natural killer cells by the presence of a special receptor on their cell surface called T cell receptor (TCR). The thymus is the principal organ responsible for the maturation of T cells. Several different subsets of T cells have been discovered, each with a distinct function.

T helper cells assist other white blood cells in immunologic processes, including maturation of B cells into plasma cells and activation of cytotoxic T cells and macrophages, among other functions. These cells are also known as CD4+ T cells because they express the CD4 protein on their surface. Helper T cells become activated when they are presented with peptide antigens by MHC class II molecules that are expressed on the surface of antigen presenting cells (APCs). Once activated, they divide rapidly and secrete small proteins called cytokines that regulate or assist in the active immune response.

Cytotoxic T cells destroy virally infected cells and tumor cells, and are also implicated in transplant rejection. These cells are also known as CD8+ T cells since they express the CD8 glycoprotein at their surface. These cells recognize their targets by binding to antigen associated with MHC class I, which is present on the surface of nearly every cell of the body.

A majority of T cells have a T cell receptor (TCR) existing as a complex of several proteins. The actual T cell receptor is composed of two separate peptide chains, which are produced from the independent T cell receptor alpha and beta (TCRα and TCRβ) genes and are called α- and β-TCR chains. γδ T cells (gamma delta T cells) represent a small subset of T cells that possess a distinct T cell receptor (TCR) on their surface. However, in γδ T cells, the TCR is made up of one γ-chain and one δ-chain. This group of T cells is much less common (2% of total T cells) than the αβ T cells.

According to the invention the term "antigen receptor" includes naturally occurring receptors such as T cell receptors as well as engineered receptors, which confer an arbitrary specificity such as the specificity of a monoclonal antibody onto an effector cell such as a T cell. In this way, a large number of antigen-specific T cells can be generated for adoptive cell transfer. Thus, an antigen receptor according to the invention may be present on T cells, e.g. instead of or in addition to the T cell's own T cell receptor. Such T cells do not necessarily require processing and presentation of an antigen for recognition of the target cell but rather may recognize preferably with specificity any antigen present on a target cell. Preferably, said antigen receptor is expressed on the surface of the cells. For the purpose of the present invention T cells comprising engineered antigen receptor are comprised by the term "T cell" as used herein. Specifically, according to the invention, the term "antigen receptor" includes artificial receptors comprising a single molecule or a complex of molecules which recognize, i.e. bind to, a target structure (e.g. an antigen) on a target cell such as a cancer cell (e.g. by binding of an antigen binding site or antigen binding domain to an antigen expressed on the surface of the target cell) and may confer specificity onto an effector cell such as a T cell expressing said antigen receptor on the cell surface. Preferably, recognition of the target structure by an antigen receptor results in activation of an effector cell expressing said antigen receptor. According to the invention an "antigen receptor" may be a "chimeric antigen receptor (CAR)", "chimeric T cell receptor" or "artificial T cell receptor".

According to the invention, antigen can be recognized by an antigen receptor through any antigen recognition domains (herein also referred to simply as "domains") able to form an antigen binding site such as through antigen-binding portions of antibodies and T cell receptors which may reside on the same or different peptide chains. In one embodiment, the two domains forming an antigen binding site are derived from an immunoglobulin. In another embodiment, the two domains forming an antigen binding site are derived from a T cell receptor. Particularly preferred are antibody variable domains, such as single-chain variable fragments (scFv) derived from monoclonal antibodies and T cell receptor variable domains, in particular TCR alpha and beta single chains. In fact almost anything that binds a given target with high affinity can be used as an antigen recognition domain.

The first signal in activation of T cells is provided by binding of the T cell receptor to a short peptide presented by the MHC on another cell. This ensures that only a T cell with a TCR specific to that peptide is activated. The partner cell is usually an antigen presenting cell such as a professional antigen presenting cell, usually a dendritic cell in the case of naïve responses, although B cells and macrophages can be important APCs.

According to the present invention, a molecule is capable of binding to a target if it has a significant affinity for said predetermined target and binds to said predetermined target in standard assays. "Affinity" or "binding affinity" is often measured by equilibrium dissociation constant ($K_D$). A molecule is not (substantially) capable of binding to a target if it has no significant affinity for said target and does not bind significantly to said target in standard assays.

Cytotoxic T lymphocytes may be generated in vivo by incorporation of an antigen or a peptide fragment thereof into antigen-presenting cells in vivo. The antigen or a peptide fragment thereof may be represented as protein, as DNA (e.g. within a vector) or as RNA. The antigen may be processed to produce a peptide partner for the MHC molecule, while a fragment thereof may be presented without the need for further processing. The latter is the case in particular, if these can bind to MHC molecules. In general, administration to a patient by intradermal injection is possible. However, injection may also be carried out intranodally into a lymph node (Maloy et al. (2001), Proc Natl Acad Sci USA 98:3299-303). The resulting cells present the complex of interest and are recognized by autologous cytotoxic T lymphocytes which then propagate.

Specific activation of CD4+ or CD8+ T cells may be detected in a variety of ways. Methods for detecting specific T cell activation include detecting the proliferation of T cells, the production of cytokines (e.g., lymphokines), or the generation of cytolytic activity. For CD4+ T cells, a preferred method for detecting specific T cell activation is the detection of the proliferation of T cells. For CD8+ T cells, a preferred method for detecting specific T cell activation is the detection of the generation of cytolytic activity.

The term "immunologically equivalent" means that the immunologically equivalent molecule such as the immunologically equivalent amino acid sequence exhibits the same or essentially the same immunological properties and/or exerts the same or essentially the same immunological effects, e.g., with respect to the type of the immunological effect such as induction of a humoral and/or cellular immune response, the strength and/or duration of the induced immune reaction, or the specificity of the induced immune reaction. In the context of the present invention, the term "immunologically equivalent" is preferably used with respect to the immunological effects or properties of a peptide used for immunization. For example, an amino acid sequence is immunologically equivalent to a reference amino acid sequence if said amino acid sequence when exposed to the immune system of a subject induces an immune reaction having a specificity of reacting with the reference amino acid sequence.

The term "immune effector functions" in the context of the present invention includes any functions mediated by components of the immune system that result, for example, in the killing of tumor cells, or in the inhibition of tumor growth and/or inhibition of tumor development, including inhibition of tumor dissemination and metastasis. Preferably, the immune effector functions in the context of the present invention are T cell mediated effector functions. Such functions comprise in the case of a helper T cell (CD4$^+$ T cell) the recognition of an antigen or an antigen fragment in the context of MHC class II molecules by T cell receptors, the release of cytokines and/or the activation of CD8$^+$ lymphocytes (CTLs) and/or B-cells, and in the case of CTL the recognition of an antigen or an antigen fragment in the context of MHC class I molecules by T cell receptors, the elimination of cells presented in the context of MHC class I molecules, i.e., cells characterized by presentation of an antigen with class I MHC, for example, via apoptosis or perforin-mediated cell lysis, production of cytokines such as IFN-γ and TNF-α, and specific cytolytic killing of antigen expressing target cells.

In general, according to the invention, proteins which are expressed by diseased cells are assessed with respect to their usefulness in immunotherapy. A protein with predicted usefulness for immunotherapy may be used for providing a vaccine comprising the protein or one or more peptide fragments thereof, in particular one or more (potential) MHC binding peptides of the protein.

According to the invention, the term "distribution" refers to a localization status. The term "ascertaining the distribution or localization", in particular, comprises a determination or prediction of the localization status, e.g. a determination or prediction of the subcellular localization or abundance of a peptide, protein or nucleic acid such as a determination or prediction of whether or not a peptide, protein or nucleic acid is located or abundant in the cytosol and/or within exosomes in vivo.

Terms such as "predict", "predicting" or "prediction" relate to the determination of a likelihood.

According to the invention, predicting the usefulness of a protein or a fragment thereof expressed by diseased cells for immunotherapy may comprise one or more of the following: (i) ascertaining the distribution or localization of the protein or a nucleic acid coding therefor, or of a fragment of the protein such as ascertaining whether the protein or a nucleic acid coding therefor, or a fragment of the protein is located or abundant in the cytosol and/or within exosomes in vivo, (ii) ascertaining whether the protein or a fragment thereof is cross-presented by antigen presenting cells, preferably professional antigen presenting cells, (iii) ascertaining an existing antibody response to the protein or a fragment thereof, (iv) ascertaining whether the protein or a fragment thereof binds to F actin, (v) ascertaining whether the protein or a fragment thereof binds to RNA In one embodiment, ascertaining whether a protein or a nucleic acid coding therefor, or a fragment of the protein is located or abundant within exosomes in vivo is performed by obtaining a sample of extracellular fluids, isolating exosomes for example by differential centrifugation, isolating proteins or nucleic acids for example by gel elecetrophoresis and identifying said protein or a fragment thereof for example via mass spectrometry, ELISA, flow cytometry, antibody array or western blotting or identifying a nucleic acid coding for said protein e.g. via microarray, RNA sequencing or RT-PCR. In another embodiment, ascertaining whether a protein or a nucleic acid coding therefor, or a fragment of the protein is located or abundant within exosomes in vivo is performed by extracting the information from a data base collecting data from experiments as described in this section above as for example ExoCarta (Keerthikumar, S, et al., J. Mol. Biol. 428, 688(2016)).

In one embodiment, ascertaining an existing antibody response can be performed using SEREX. SEREX means serological identification of antigens by recombinant expression cloning and is a method to identify tumor antigens by screening of antibodies from patients sera for the recognition of a tumor-derived cDNA transduced phage library. This technique uses a phage display library to express a large variety of potential antigens of a patient. The antigens are transferred to a two-dimensional surface allowing their mapping to specific clones. The surface is incubated with autologous patient sera. Immune reactive clones are located, cultivated and sequenced (Sahin, U, et al., PNAS 92, 11810 (1995)).

The present invention also may comprise breaking of protein sequences into appropriate fragments for MHC binding and ascertaining scores for binding of the fragments to one or more MHC molecules. Outputs may be ranked and may consist of a list of peptides and their predicted scores, indicating their likelihood of binding. In general, proteins according to the invention are particularly useful for immunotherapy if they contain one or more (potential) MHC binding peptides.

The methods of the invention may be performed for a patient such as a cancer patient, for example, on a tumor specimen of a patient such as a cancer patient.

According to the invention, a protein or protein fragment described herein preferably contains at least one amino acid modification. The amino acid modifications the usefulness for immunotherapy of which is to be determined according to the present invention or which are to be selected and/or ranked according to their predicted immunogenicity according to the invention may result from mutations in the nucleic acid of a cell. Such mutations may be identified by known sequencing techniques.

In one embodiment, the mutations are cancer specific somatic mutations in a tumor specimen of a cancer patient which may be determined by identifying sequence differences between the genome, exome and/or transcriptome of a tumor specimen and the genome, exome and/or transcriptome of a non-tumorigenous specimen.

According to the invention a tumor specimen relates to any sample such as a bodily sample derived from a patient containing or being expected of containing tumor or cancer cells. The bodily sample may be any tissue sample such as blood, a tissue sample obtained from the primary tumor or from tumor metastases or any other sample containing tumor or cancer cells. Preferably, a bodily sample is blood and cancer specific somatic mutations or sequence differences are determined in one or more circulating tumor cells (CTCs) contained in the blood.

In another embodiment, a tumor specimen relates to one or more isolated tumor or cancer cells such as circulating tumor cells (CTCs) or a sample containing one or more isolated tumor or cancer cells such as circulating tumor cells (CTCs).

A non-tumorigenous specimen relates to any sample such as a bodily sample derived from a patient or another individual which preferably is of the same species as the patient, preferably a healthy individual not containing or not being expected of containing tumor or cancer cells. The bodily sample may be any tissue sample such as blood or a sample from a non-tumorigenous tissue.

The invention may involve the determination of the cancer mutation signature of a patient. The term "cancer mutation signature" may refer to all cancer mutations present in one or more cancer cells of a patient or it may refer to only a portion of the cancer mutations present in one or more cancer cells of a patient. Accordingly, the present invention may involve the identification of all cancer specific mutations present in one or more cancer cells of a patient or it may involve the identification of only a portion of the cancer specific mutations present in one or more cancer cells of a patient. Generally, the methods of the invention provides for the identification of a number of mutations which provides a sufficient number of modifications or modified proteins to be included in the methods of the invention.

Preferably, the mutations identified according to the present invention are non-synonymous mutations, preferably non-synonymous mutations of proteins expressed in a tumor or cancer cell.

In one embodiment, cancer specific somatic mutations or sequence differences are determined in the genome, preferably the entire genome, of a tumor specimen. Thus, the invention may comprise identifying the cancer mutation signature of the genome, preferably the entire genome of one or more cancer cells. In one embodiment, the step of identifying cancer specific somatic mutations in a tumor specimen of a cancer patient comprises identifying the genome-wide cancer mutation profile.

In one embodiment, cancer specific somatic mutations or sequence differences are determined in the exome, preferably the entire exome, of a tumor specimen. Thus, the invention may comprise identifying the cancer mutation signature of the exome, preferably the entire exome of one or more cancer cells. In one embodiment, the step of identifying cancer specific somatic mutations in a tumor specimen of a cancer patient comprises identifying the exome-wide cancer mutation profile.

In one embodiment, cancer specific somatic mutations or sequence differences are determined in the transcriptome, preferably the entire transcriptome, of a tumor specimen. Thus, the invention may comprise identifying the cancer mutation signature of the transcriptome, preferably the entire transcriptome of one or more cancer cells. In one embodiment, the step of identifying cancer specific somatic mutations in a tumor specimen of a cancer patient comprises identifying the transcriptome-wide cancer mutation profile.

In one embodiment, the step of identifying cancer specific somatic mutations or identifying sequence differences comprises single cell sequencing of one or more, preferably 2, 3, 4, 5, 6, 7, 8, 9, 10, 11, 12, 13, 14, 15, 16, 17, 18, 19, 20 or even more cancer cells. Thus, the invention may comprise identifying a cancer mutation signature of said one or more cancer cells. In one embodiment, the cancer cells are circulating tumor cells. The cancer cells such as the circulating tumor cells may be isolated prior to single cell sequencing.

In one embodiment, the step of identifying cancer specific somatic mutations or identifying sequence differences involves using next generation sequencing (NGS).

In one embodiment, the step of identifying cancer specific somatic mutations or identifying sequence differences comprises sequencing genomic DNA and/or RNA of the tumor specimen.

To reveal cancer specific somatic mutations or sequence differences the sequence information obtained from the tumor specimen is preferably compared with a reference such as sequence information obtained from sequencing nucleic acid such as DNA or RNA of normal non-cancerous cells such as germline cells which may either be obtained from the patient or a different individual. In one embodiment, normal genomic germline DNA is obtained from peripheral blood mononuclear cells (PBMCs)

The term "genome" relates to the total amount of genetic information in the chromosomes of an organism or a cell.

The term "exome" refers to part of the genome of an organism formed by exons, which are coding portions of expressed genes. The exome provides the genetic blueprint used in the synthesis of proteins and other functional gene products. It is the most functionally relevant part of the genome and, therefore, it is most likely to contribute to the phenotype of an organism. The exome of the human genome is estimated to comprise 1.5% of the total genome (Ng, P C et al., *PLoS Gen.*, 4(8): 1-15, 2008).

The term "transcriptome" relates to the set of all RNA molecules, including mRNA, rRNA, tRNA, and other non-coding RNA produced in one cell or a population of cells. In context of the present invention the transcriptome means the set of all RNA molecules produced in one cell, a population of cells, preferably a population of cancer cells, or all cells of a given individual at a certain time point.

A "nucleic acid" is according to the invention preferably deoxyribonucleic acid (DNA) or ribonucleic acid (RNA), more preferably RNA, most preferably in vitro transcribed RNA (IVT RNA) or synthetic RNA. Nucleic acids include according to the invention genomic DNA, cDNA, mRNA, recombinantly produced and chemically synthesized molecules. According to the invention, a nucleic acid may be present as a single-stranded or double-stranded and linear or covalently circularly closed molecule. A nucleic acid can, according to the invention, be isolated. The term "isolated nucleic acid" means, according to the invention, that the nucleic acid (i) was amplified in vitro, for example via polymerase chain reaction (PCR), (ii) was produced recombinantly by cloning, (iii) was purified, for example, by cleavage and separation by gel electrophoresis, or (iv) was synthesized, for example, by chemical synthesis. A nucleic can be employed for introduction into, i.e. transfection of, cells, in particular, in the form of RNA which can be prepared by in vitro transcription from a DNA template. The RNA can moreover be modified before application by stabilizing sequences, capping, and polyadenylation.

The term "genetic material" refers to isolated nucleic acid, either DNA or RNA, a section of a double helix, a section of a chromosome, or an organism's or cell's entire genome, in particular its exome or transcriptome.

The term "mutation" refers to a change of or difference in the nucleic acid sequence (nucleotide substitution, addition or deletion) compared to a reference. A "somatic mutation" can occur in any of the cells of the body except the germ cells (sperm and egg) and therefore are not passed on to children. These alterations can (but do not always) cause cancer or other diseases. Preferably a mutation is a non-synonymous mutation. The term "non-synonymous mutation" refers to a mutation, preferably a nucleotide substitution, which does result in an amino acid change such as an amino acid substitution in the translation product.

According to the invention, the term "mutation" includes point mutations, Indels, fusions, chromothripsis and RNA edits.

According to the invention, the term "Indel" describes a special mutation class, defined as a mutation resulting in a colocalized insertion and deletion and a net gain or loss in nucleotides. In coding regions of the genome, unless the length of an indel is a multiple of 3, they produce a frameshift mutation. Indels can be contrasted with a point mutation; where an Indel inserts and deletes nucleotides from a sequence, a point mutation is a form of substitution that replaces one of the nucleotides.

Fusions can generate hybrid genes formed from two previously separate genes. It can occur as the result of a translocation, interstitial deletion, or chromosomal inversion. Often, fusion genes are oncogenes. Oncogenic fusion genes may lead to a gene product with a new or different function from the two fusion partners. Alternatively, a proto-oncogene is fused to a strong promoter, and thereby the oncogenic function is set to function by an upregulation caused by the strong promoter of the upstream fusion partner. Oncogenic fusion transcripts may also be caused by trans-splicing or read-through events.

According to the invention, the term "chromothripsis" refers to a genetic phenomenon by which specific regions of the genome are shattered and then stitched together via a single devastating event.

According to the invention, the term "RNA edit" or "RNA editing" refers to molecular processes in which the information content in an RNA molecule is altered through a chemical change in the base makeup. RNA editing includes nucleoside modifications such as cytidine (C) to uridine (U) and adenosine (A) to inosine (I) deaminations, as well as non-templated nucleotide additions and insertions. RNA editing in mRNAs effectively alters the amino acid sequence of the encoded protein so that it differs from that predicted by the genomic DNA sequence.

The term "cancer mutation signature" refers to a set of mutations which are present in cancer cells when compared to non-cancerous reference cells.

According to the invention, a "reference" may be used to correlate and compare the results from a tumor specimen. Typically the "reference" may be obtained on the basis of one or more normal specimens, in particular specimens which are not affected by a cancer disease, either obtained from a patient or one or more different individuals, preferably healthy individuals, in particular individuals of the same species. A "reference" can be determined empirically by testing a sufficiently large number of normal specimens.

Any suitable sequencing method can be used according to the invention for determining mutations, Next Generation Sequencing (NGS) technologies being preferred. Third Generation Sequencing methods might substitute for the NGS technology in the future to speed up the sequencing step of the method. For clarification purposes: the terms "Next Generation Sequencing" or "NGS" in the context of the present invention mean all novel high throughput sequencing technologies which, in contrast to the "conventional" sequencing methodology known as Sanger chemistry, read nucleic acid templates randomly in parallel along the entire genome by breaking the entire genome into small pieces. Such NGS technologies (also known as massively parallel sequencing technologies) are able to deliver nucleic acid sequence information of a whole genome, exome, transcriptome (all transcribed sequences of a genome) or methylome (all methylated sequences of a genome) in very short time periods, e.g. within 1-2 weeks, preferably within 1-7 days or most preferably within less than 24 hours and allow, in principle, single cell sequencing approaches. Multiple NGS platforms which are commercially available or which are mentioned in the literature can be used in the context of the present invention e.g. those described in detail in Zhang et al. 2011: *The impact of next-generation sequencing on genomics. J. Genet Genomics* 38 (3), 95-109; or in Voelkerding et al. 2009: *Next generation sequencing: From basic research to diagnostics. Clinical chemistry* 55, 641-658. Non-limiting examples of such NGS technologies/platforms are 1) The sequencing-by-synthesis technology known as pyrosequencing implemented e.g. in the GS-FLX 454 Genome Sequencer™ of Roche-associated company 454 Life Sciences (Branford, Connecticut), first described in Ronaghi et al. 1998: *A sequencing method based on real-time pyrophosphate". Science* 281 (5375), 363-365. This technology uses an emulsion PCR in which single-stranded DNA binding beads are encapsulated by vigorous vortexing into aqueous micelles containing PCR reactants surrounded by oil for emulsion PCR amplification. During the pyrosequencing process, light emitted from phosphate molecules during nucleotide incorporation is recorded as the polymerase synthesizes the DNA strand.

2) The sequencing-by-synthesis approaches developed by Solexa (now part of Illumina Inc., San Diego, California) which is based on reversible dye-terminators and implemented e.g. in the Illumina/Solexa Genome Analyzer™ and in the Illumina HiSeq 2000 Genome Analyzer™. In this technology, all four nucleotides are added simultaneously into oligo-primed cluster fragments in flow-cell channels along with DNA polymerase. Bridge amplification extends cluster strands with all four fluorescently labeled nucleotides for sequencing.

3) Sequencing-by-ligation approaches, e.g. implemented in the SOLid™ platform of Applied Biosystems (now Life Technologies Corporation, Carlsbad, California). In this technology, a pool of all possible oligonucleotides of a fixed length are labeled according to the sequenced position. Oligonucleotides are annealed and ligated; the preferential ligation by DNA ligase for matching sequences results in a signal informative of the nucleotide at that position. Before sequencing, the DNA is amplified by emulsion PCR. The resulting bead, each containing only copies of the same DNA molecule, are deposited on a glass slide. As a second example, he Polonator™ G.007 platform of Dover Systems (Salem, New Hampshire) also employs a sequencing-by-ligation approach by using a randomly arrayed, bead-based, emulsion PCR to amplify DNA fragments for parallel sequencing.

4) Single-molecule sequencing technologies such as e.g. implemented in the PacBio RS system of Pacific Biosciences (Menlo Park, California) or in the HeliScope™ platform of Helicos Biosciences (Cambridge, Massachusetts). The distinct characteristic of this technology is its ability to sequence single DNA or RNA molecules without amplification, defined as Single-Molecule Real Time (SMRT) DNA sequencing. For example, HeliScope uses a highly sensitive fluorescence detection system to directly detect each nucleotide as it is synthesized. A similar approach based on fluorescence resonance energy transfer (FRET) has been developed from Visigen Biotechnology (Houston, Texas). Other fluorescence-based single-molecule techniques are from U.S. Genomics (GeneEngine™) and Genovoxx (AnyGene™).

5) Nano-technologies for single-molecule sequencing in which various nanostructures are used which are e.g. arranged on a chip to monitor the movement of a polymerase molecule on a single strand during replication. Non-limiting examples for approaches based on nano-technologies are the GridON™ platform of Oxford Nanopore Technologies (Oxford, UK), the hybridization-assisted nano-pore sequencing (HANS™) platforms developed by Nabsys (Providence, Rhode Island), and the proprietary ligase-based DNA sequencing platform with DNA nanoball (DNB) technology called combinatorial probe-anchor ligation (cPAL™).

6) Electron microscopy based technologies for single-molecule sequencing, e.g. those developed by Light-Speed Genomics (Sunnyvale, California) and Halcyon Molecular (Redwood City, California)

7) Ion semiconductor sequencing which is based on the detection of hydrogen ions that are released during the polymerisation of DNA. For example, Ion Torrent Systems (San Francisco, California) uses a high-density array of micro-machined wells to perform this biochemical process in a massively parallel way. Each well holds a different DNA template. Beneath the wells is an ion-sensitive layer and beneath that a proprietary Ion sensor.

Preferably, DNA and RNA preparations serve as starting material for NGS. Such nucleic acids can be easily obtained from samples such as biological material, e.g. from fresh, flash-frozen or formalin-fixed paraffin embedded tumor tissues (FFPE) or from freshly isolated cells or from CTCs which are present in the peripheral blood of patients. Normal non-mutated genomic DNA or RNA can be extracted from normal, somatic tissue, however germline cells are preferred in the context of the present invention. Germline DNA or RNA may be extracted from peripheral blood mononuclear cells (PBMCs) in patients with non-hematological malignancies. Although nucleic acids extracted from FFPE tissues or freshly isolated single cells are highly fragmented, they are suitable for NGS applications.

Several targeted NGS methods for exome sequencing are described in the literature (for review see e.g. Teer and Mullikin 2010: *Human Mol Genet* 19 (2), R145-51), all of which can be used in conjunction with the present invention. Many of these methods (described e.g. as genome capture, genome partitioning, genome enrichment etc.) use hybridization techniques and include array-based (e.g. Hodges et al. 2007: *Nat. Genet.* 39, 1522-1527) and liquid-based (e.g. Choi et al. 2009: *Proc. Natl. Acad. Sci USA* 106, 19096-19101) hybridization approaches. Commercial kits for DNA sample preparation and subsequent exome capture are also available: for example, Illumina Inc. (San Diego, California) offers the TruSeq™ DNA Sample Preparation Kit and the Exome Enrichment Kit TruSeq™ Exome Enrichment Kit.

In order to reduce the number of false positive findings in detecting cancer specific somatic mutations or sequence differences when comparing e.g. the sequence of a tumor sample to the sequence of a reference sample such as the sequence of a germ line sample it is preferred to determine the sequence in replicates of one or both of these sample types. Thus, it is preferred that the sequence of a reference sample such as the sequence of a germ line sample is determined twice, three times or more. Alternatively or additionally, the sequence of a tumor sample is determined twice, three times or more. It may also be possible to determine the sequence of a reference sample such as the sequence of a germ line sample and/or the sequence of a tumor sample more than once by determining at least once the sequence in genomic DNA and determining at least once the sequence in RNA of said reference sample and/or of said tumor sample. For example, by determining the variations between replicates of a reference sample such as a germ line sample the expected rate of false positive (FDR) somatic mutations as a statistical quantity can be estimated. Technical repeats of a sample should generate identical results and any detected mutation in this "same vs. same comparison" is a false positive. In particular, to determine the false discovery rate for somatic mutation detection in a tumor sample relative to a reference sample, a technical repeat of the reference sample can be used as a reference to estimate the number of false positives. Furthermore, various quality related metrics (e.g. coverage or SNP quality) may be combined into a single quality score using a machine learning approach. For a given somatic variation all other variations with an exceeding quality score may be counted, which enables a ranking of all variations in a dataset.

In the context of the present invention, the term "RNA" relates to a molecule which comprises at least one ribonucleotide residue and preferably being entirely or substantially composed of ribonucleotide residues. "Ribonucleotide" relates to a nucleotide with a hydroxyl group at the 2'-position of a β-D-ribofuranosyl group. The term "RNA" comprises double-stranded RNA, single-stranded RNA, isolated RNA such as partially or completely purified RNA, essentially pure RNA, synthetic RNA, and recombinantly generated RNA such as modified RNA which differs from naturally occurring RNA by addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

According to the present invention, the term "RNA" includes and preferably relates to "mRNA". The term "mRNA" means "messenger-RNA" and relates to a "transcript" which is generated by using a DNA template and encodes a peptide or polypeptide. Typically, an mRNA comprises a 5'-UTR, a protein coding region, a 3'-UTR and optionally a poly(A) tail. mRNA only possesses limited half-life in cells and in vitro. In the context of the present invention, mRNA may be generated by in vitro transcription from a DNA template. The in vitro transcription methodology is known to the skilled person. For example, there is a variety of in vitro transcription kits commercially available.

According to the invention, the stability and translation efficiency of RNA may be modified as required. For example, RNA may be stabilized and its translation increased by one or more modifications having a stabilizing effects and/or increasing translation efficiency of RNA. Such modifications are described, for example, in PCT/EP2006/009448 incorporated herein by reference. In order to increase expression of the RNA used according to the present invention, it may be modified within the coding region, i.e. the sequence encoding the expressed peptide or protein, preferably without altering the sequence of the expressed peptide or protein, so as to increase the GC-content to increase mRNA stability and to perform a codon optimization and, thus, enhance translation in cells.

The term "modification" in the context of the RNA used in the present invention includes any modification of an RNA which is not naturally present in said RNA.

In one embodiment of the invention, the RNA used according to the invention does not have uncapped 5'-triphosphates. Removal of such uncapped 5'-triphosphates can be achieved by treating RNA with a phosphatase.

The RNA according to the invention may have modified ribonucleotides in order to increase its stability and/or decrease cytotoxicity. For example, in one embodiment, in the RNA used according to the invention 5-methylcytidine is substituted partially or completely, preferably completely, for cytidine. Alternatively or additionally, in one embodiment, in the RNA used according to the invention pseudouridine is substituted partially or completely, preferably completely, for uridine.

In one embodiment, the term "modification" relates to providing an RNA with a 5'-cap or 5'-cap analog. The term "5'-cap" refers to a cap structure found on the 5'-end of an mRNA molecule and generally consists of a guanosine nucleotide connected to the mRNA via an unusual 5' to 5' triphosphate linkage. In one embodiment, this guanosine is methylated at the 7-position. The term "conventional 5'-cap" refers to a naturally occurring RNA 5'-cap, preferably to the 7-methylguanosine cap ($m^7G$). In the context of the present invention, the term "5'-cap" includes a 5'-cap analog that resembles the RNA cap structure and is modified to possess the ability to stabilize RNA and/or enhance translation of RNA if attached thereto, preferably in vivo and/or in a cell.

Providing an RNA with a 5'-cap or 5'-cap analog may be achieved by in vitro transcription of a DNA template in presence of said 5'-cap or 5'-cap analog, wherein said 5'-cap is co-transcriptionally incorporated into the generated RNA strand, or the RNA may be generated, for example, by in vitro transcription, and the 5'-cap may be attached to the RNA post-transcriptionally using capping enzymes, for example, capping enzymes of vaccinia virus.

The RNA may comprise further modifications. For example, a further modification of the RNA used in the present invention may be an extension or truncation of the naturally occurring poly(A) tail or an alteration of the 5'- or 3'-untranslated regions (UTR) such as introduction of a UTR which is not related to the coding region of said RNA, for example, the exchange of the existing 3'-UTR with or the insertion of one or more, preferably two copies of a 3'-UTR derived from a globin gene, such as alpha2-globin, alpha1-globin, beta-globin, preferably beta-globin, more preferably human beta-globin.

RNA having an unmasked poly-A sequence is translated more efficiently than RNA having a masked poly-A sequence. The term "poly(A) tail" or "poly-A sequence" relates to a sequence of adenyl (A) residues which typically is located on the 3'-end of a RNA molecule and "unmasked poly-A sequence" means that the poly-A sequence at the 3' end of an RNA molecule ends with an A of the poly-A sequence and is not followed by nucleotides other than A located at the 3' end, i.e. downstream, of the poly-A sequence. Furthermore, a long poly-A sequence of about 120 base pairs results in an optimal transcript stability and translation efficiency of RNA.

Therefore, in order to increase stability and/or expression of the RNA used according to the present invention, it may be modified so as to be present in conjunction with a poly-A sequence, preferably having a length of 10 to 500, more preferably 30 to 300, even more preferably 65 to 200 and especially 100 to 150 adenosine residues. In an especially preferred embodiment the poly-A sequence has a length of approximately 120 adenosine residues. To further increase stability and/or expression of the RNA used according to the invention, the poly-A sequence can be unmasked.

In addition, incorporation of a 3'-non translated region (UTR) into the 3'-non translated region of an RNA molecule can result in an enhancement in translation efficiency. A synergistic effect may be achieved by incorporating two or more of such 3'-non translated regions. The 3'-non translated regions may be autologous or heterologous to the RNA into which they are introduced. In one particular embodiment the 3'-non translated region is derived from the human β-globin gene.

A combination of the above described modifications, i.e. incorporation of a poly-A sequence, unmasking of a poly-A sequence and incorporation of one or more 3'-non translated regions, has a synergistic influence on the stability of RNA and increase in translation efficiency.

The term "stability" of RNA relates to the "half-life" of RNA. "Half-life" relates to the period of time which is needed to eliminate half of the activity, amount, or number of molecules. In the context of the present invention, the half-life of an RNA is indicative for the stability of said RNA. The half-life of RNA may influence the "duration of expression" of the RNA. It can be expected that RNA having a long half-life will be expressed for an extended time period.

Of course, if according to the present invention it is desired to decrease stability and/or translation efficiency of RNA, it is possible to modify RNA so as to interfere with the function of elements as described above increasing the stability and/or translation efficiency of RNA.

The term "expression" is used according to the invention in its most general meaning and comprises the production of RNA and/or peptides, polypeptides or proteins, e.g. by transcription and/or translation. With respect to RNA, the term "expression" or "translation" relates in particular to the production of peptides, polypeptides or proteins. It also comprises partial expression of nucleic acids. Moreover, expression can be transient or stable.

According to the invention, the term expression also includes an "aberrant expression" or "abnormal expression". "Aberrant expression" or "abnormal expression" means according to the invention that expression is altered, preferably increased, compared to a reference, e.g. a state in a subject not having a disease associated with aberrant or abnormal expression of a certain protein, e.g., a tumor antigen. An increase in expression refers to an increase by at least 10%, in particular at least 20%, at least 50% or at least 100%, or more. In one embodiment, expression is only found in a diseased tissue, while expression in a healthy tissue is repressed.

The term "specifically expressed" means that a protein is essentially only expressed in a specific tissue or organ. For example, a tumor antigen specifically expressed in gastric mucosa means that said protein is primarily expressed in gastric mucosa and is not expressed in other tissues or is not expressed to a significant extent in other tissue or organ types. Thus, a protein that is exclusively expressed in cells of the gastric mucosa and to a significantly lesser extent in any other tissue, such as testis, is specifically expressed in cells of the gastric mucosa. In some embodiments, a tumor antigen may also be specifically expressed under normal conditions in more than one tissue type or organ, such as in 2 or 3 tissue types or organs, but preferably in not more than 3 different tissue or organ types. In this case, the tumor antigen is then specifically expressed in these organs. For example, if a tumor antigen is expressed under normal conditions preferably to an approximately equal extent in lung and stomach, said tumor antigen is specifically expressed in lung and stomach.

In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector". According to the present invention, the RNA used in the present invention preferably is in vitro transcribed RNA (IVT-RNA) and may be obtained by in vitro transcription of an appropriate DNA template. The promoter for controlling transcription can be any promoter for any RNA polymerase. Particular examples of RNA polymerases are the T7, T3, and SP6 RNA polymerases. Preferably, the in vitro transcription according to the invention is controlled by a T7 or SP6 promoter. A DNA template for in vitro transcription may be obtained by cloning of a nucleic acid, in particular cDNA, and introducing it into an appropriate vector for in vitro transcription. The cDNA may be obtained by reverse transcription of RNA.

The term "translation" according to the invention relates to the process in the ribosomes of a cell by which a strand of messenger RNA directs the assembly of a sequence of amino acids to make a peptide, polypeptide or protein.

Expression control sequences or regulatory sequences, which according to the invention may be linked functionally with a nucleic acid, can be homologous or heterologous with respect to the nucleic acid. A coding sequence and a regulatory sequence are linked together "functionally" if they are bound together covalently, so that the transcription or translation of the coding sequence is under the control or under the influence of the regulatory sequence. If the coding sequence is to be translated into a functional protein, with functional linkage of a regulatory sequence with the coding sequence, induction of the regulatory sequence leads to a transcription of the coding sequence, without causing a reading frame shift in the coding sequence or inability of the coding sequence to be translated into the desired protein or peptide.

The term "expression control sequence" or "regulatory sequence" comprises, according to the invention, promoters, ribosome-binding sequences and other control elements, which control the transcription of a nucleic acid or the translation of the derived RNA. In certain embodiments of the invention, the regulatory sequences can be controlled. The precise structure of regulatory sequences can vary depending on the species or depending on the cell type, but generally comprises 5'-untranscribed and 5'- and 3'-untranslated sequences, which are involved in the initiation of transcription or translation, such as TATA-box, capping-sequence, CAAT-sequence and the like. In particular, 5'-untranscribed regulatory sequences comprise a promoter region that includes a promoter sequence for transcriptional control of the functionally bound gene. Regulatory sequences can also comprise enhancer sequences or upstream activator sequences.

Preferably, according to the invention, RNA to be expressed in a cell is introduced into said cell. In one embodiment of the methods according to the invention, the RNA that is to be introduced into a cell is obtained by in vitro transcription of an appropriate DNA template.

According to the invention, terms such as "RNA capable of expressing" and "RNA encoding" are used interchangeably herein and with respect to a particular peptide or polypeptide mean that the RNA, if present in the appropriate environment, preferably within a cell, can be expressed to produce said peptide or polypeptide. Preferably, RNA according to the invention is able to interact with the cellular translation machinery to provide the peptide or polypeptide it is capable of expressing.

Terms such as "transferring", "introducing" or "transfecting" are used interchangeably herein and relate to the introduction of nucleic acids, in particular exogenous or heterologous nucleic acids, in particular RNA into a cell. According to the present invention, the cell can form part of an organ, a tissue and/or an organism. According to the present invention, the administration of a nucleic acid is either achieved as naked nucleic acid or in combination with an administration reagent. Preferably, administration of nucleic acids is in the form of naked nucleic acids. Preferably, the RNA is administered in combination with stabilizing substances such as RNase inhibitors. The present invention also envisions the repeated introduction of nucleic acids into cells to allow sustained expression for extended time periods.

Cells can be transfected with any carriers with which RNA can be associated, e.g. by forming complexes with the RNA or forming vesicles in which the RNA is enclosed or encapsulated, resulting in increased stability of the RNA compared to naked RNA. Carriers useful according to the invention include, for example, lipid-containing carriers such as cationic lipids, liposomes, in particular cationic liposomes, and micelles, and nanoparticles. Cationic lipids may form complexes with negatively charged nucleic acids. Any cationic lipid may be used according to the invention.

Preferably, the introduction of RNA which encodes a peptide or polypeptide into a cell, in particular into a cell present in vivo, results in expression of said peptide or polypeptide in the cell. In particular embodiments, the targeting of the nucleic acids to particular cells is preferred. In such embodiments, a carrier which is applied for the administration of the nucleic acid to a cell (for example, a retrovirus or a liposome), exhibits a targeting molecule. For example, a molecule such as an antibody which is specific for a surface membrane protein on the target cell or a ligand for a receptor on the target cell may be incorporated into the nucleic acid carrier or may be bound thereto. In case the nucleic acid is administered by liposomes, proteins which bind to a surface membrane protein which is associated with endocytosis may be incorporated into the liposome formulation in order to enable targeting and/or uptake. Such proteins encompass capsid proteins of fragments thereof which are specific for a particular cell type, antibodies against proteins which are internalized, proteins which target an intracellular location etc.

The term "cell" or "host cell" preferably is an intact cell, i.e. a cell with an intact membrane that has not released its normal intracellular components such as enzymes, organelles, or genetic material. An intact cell preferably is a viable cell, i.e. a living cell capable of carrying out its normal metabolic functions. Preferably said term relates according to the invention to any cell which can be transformed or transfected with an exogenous nucleic acid. The term "cell" includes according to the invention prokaryotic cells (e.g., E. coli) or eukaryotic cells (e.g., dendritic cells, B cells, CHO cells, COS cells, K562 cells, HEK293 cells, HELA cells, yeast cells, and insect cells). The exogenous nucleic acid may be found inside the cell (i) freely dispersed as such, (ii) incorporated in a recombinant vector, or (iii) integrated into the host cell genome or mitochondrial DNA. Mammalian cells are particularly preferred, such as cells from humans, mice, hamsters, pigs, goats, and primates. The cells may be derived from a large number of tissue types and include primary cells and cell lines. Specific examples include keratinocytes, peripheral blood leukocytes, bone marrow stem cells, and embryonic stem cells. In further embodiments, the cell is an antigen-presenting cell, in particular a dendritic cell, a monocyte, or macrophage.

A cell which comprises a nucleic acid molecule preferably expresses the peptide or polypeptide encoded by the nucleic acid.

The term "clonal expansion" refers to a process wherein a specific entity is multiplied. In the context of the present invention, the term is preferably used in the context of an immunological response in which lymphocytes are stimulated by an antigen, proliferate, and the specific lymphocyte recognizing said antigen is amplified. Preferably, clonal expansion leads to differentiation of the lymphocytes.

Terms such as "reducing" or "inhibiting" relate to the ability to cause an overall decrease, preferably of 5% or greater, 10% or greater, 20% or greater, more preferably of 50% or greater, and most preferably of 75% or greater, in the level. The term "inhibit" or similar phrases includes a complete or essentially complete inhibition, i.e. a reduction to zero or essentially to zero.

Terms such as "increasing", "enhancing", "promoting" or "prolonging" preferably relate to an increase, enhancement, promotion or prolongation by about at least 10%, preferably at least 20%, preferably at least 30%, preferably at least 40%, preferably at least 50%, preferably at least 80%, preferably at least 100%, preferably at least 200% and in particular at least 300%. These terms may also relate to an increase, enhancement, promotion or prolongation from zero or a non-measurable or non-detectable level to a level of more than zero or a level which is measurable or detectable.

The present invention provides vaccines such as cancer vaccines designed on the basis of preferably modified proteins or protein fragments or amino acid modifications predicted as being useful in immunotherapy by the methods of the present invention.

According to the invention, the term "vaccine" relates to a pharmaceutical preparation (pharmaceutical composition) or product that upon administration induces an immune response, in particular a cellular immune response, which recognizes and attacks a pathogen or a diseased cell such as a cancer cell. A vaccine may be used for the prevention or treatment of a disease. The term "personalized cancer vaccine" or "individualized cancer vaccine" concerns a particular cancer patient and means that a cancer vaccine is adapted to the needs or special circumstances of an individual cancer patient.

In one embodiment, a vaccine provided according to the invention may comprise a peptide or polypeptide comprising one or more amino acid modifications or one or more modified peptides predicted as being useful in immunotherapy by the methods of the invention or a nucleic acid, preferably RNA, encoding said peptide or polypeptide.

The cancer vaccines provided according to the invention when administered to a patent preferably provide one or more T cell epitopes suitable for stimulating, priming and/or expanding T cells specific for diseased cells of the patient such as the patient's tumor. The T cells are preferably directed against cells expressing antigens from which the T cell epitopes are derived. The vaccines described herein are preferably capable of inducing or promoting a cellular response, preferably cytotoxic T cell activity, against a cancer disease characterized by presentation of one or more tumor-associated neo-antigens with class I MHC. A vaccine targeting cancer specific mutations will be specific for the patient's tumor.

A vaccine provided according to the invention relates to a vaccine which when administered to a patent preferably provides one or more T cell epitopes, such as 2 or more, 5 or more, 10 or more, or more, 20 or more, 25 or more, 30 or more and preferably up to 60, up to 55, up to 50, up to 45, up to 40, up to 35 or up to 30 T cell epitopes, incorporating amino acid modifications or modified peptides predicted as being immunogenic by the methods of the invention. Such T cell epitopes are also termed "neo-epitopes" herein. Presentation of these epitopes by cells of a patient, in particular antigen presenting cells, preferably results in T cells targeting the epitopes when bound to MHC and thus, the patient's tumor, preferably the primary tumor as well as tumor metastases, expressing antigens from which the T cell epitopes are derived and presenting the same epitopes on the surface of the tumor cells.

The methods of the invention may comprise the further step of determining the usability of the identified amino acid modifications or modified peptides for cancer vaccination. Thus further steps can involve one or more of the following: (i) assessing whether the modifications are located in known or predicted MHC presented epitopes, (ii) in vitro and/or in silico testing whether the modifications are located in MHC presented epitopes, e.g. testing whether the modifications are part of peptide sequences which are processed into and/or presented as MHC presented epitopes, and (iii) in vitro testing whether the envisaged modified epitopes, in particular when present in their natural sequence context, e.g. when flanked by amino acid sequences also flanking said epitopes in the naturally occurring protein, and when expressed in antigen presenting cells are able to stimulate T cells such as T cells of the patient having the desired specificity. Such flanking sequences each may comprise 3 or more, 5 or more, 10 or more, 15 or more, 20 or more and preferably up to 50, up to 45, up to 40, up to 35 or up to 30 amino acids and may flank the epitope sequence N-terminally and/or C-terminally.

Modified peptides determined according to the invention may be ranked for their usability as epitopes for cancer vaccination. Thus, in one aspect, the invention comprises a manual or computer-based analytical process in which the identified modified peptides are analyzed and selected for their usability in the respective vaccine to be provided. In a preferred embodiment, said analytical process is a computational algorithm-based process. Preferably, said analytical process comprises determining and/or ranking epitopes according to a prediction of their capacity of being immunogenic.

The neo-epitopes identified according to the invention and provided by a vaccine of the invention are preferably present in the form of a polypeptide comprising said neo-epitopes such as a polyepitopic polypeptide or a nucleic acid, in particular RNA, encoding said polypeptide. Furthermore, the neo-epitopes may be present in the polypeptide in the form of a vaccine sequence, i.e. present in their natural sequence context, e.g. flanked by amino acid sequences also flanking said epitopes in the naturally occurring protein. Such flanking sequences each may comprise 5 or more, 10 or more, 15 or more, 20 or more and preferably up to 50, up to 45, up to 40, up to 35 or up to 30 amino acids and may flank the epitope sequence N-terminally and/or C-terminally. Thus, a vaccine sequence may comprise 20 or more, 25 or more, 30 or more, 35 or more, 40 or more and preferably up to 50, up to 45, up to 40, up to 35 or up to 30 amino acids. In one embodiment, the neo-epitopes and/or vaccine sequences are lined up in the polypeptide head-to-tail.

In one embodiment, the neo-epitopes and/or vaccine sequences are spaced by linkers, in particular neutral linkers. The term "linker" according to the invention relates to a peptide added between two peptide domains such as epitopes or vaccine sequences to connect said peptide domains. There is no particular limitation regarding the linker sequence. However, it is preferred that the linker sequence reduces steric hindrance between the two peptide domains, is well translated, and supports or allows processing of the epitopes. Furthermore, the linker should have no or only little immunogenic sequence elements. Linkers preferably should not create non-endogenous neo-epitopes like those generated from the junction suture between adjacent neo-epitopes, which might generate unwanted immune reactions. Therefore, the polyepitopic vaccine should preferably contain linker sequences which are able to reduce the number of unwanted MHC binding junction epitopes. Hoyt et al. (*EMBO J.* 25(8), 1720-9, 2006) and Zhang et al. (*J. Biol. Chem.*, 279(10), 8635-41, 2004) have shown that glycine-rich sequences impair proteasomal processing and thus the use of glycine rich linker sequences act to minimize the number of linker-contained peptides that can be processed by the proteasome. Furthermore, glycine was observed to inhibit a strong binding in MHC binding groove positions (Abastado et al., *J. Immunol.* 151(7), 3569-75, 1993). Schlessinger et al. (*Proteins,* 61(1), 115-26, 2005) had found that amino acids glycine and serine included in an amino acid sequence result in a more flexible protein that is more efficiently translated and processed by the proteasome, enabling better access to the encoded neo-epitopes. The linker each may comprise 3 or more, 6 or more, 9 or more, 10 or more, 15 or more, 20 or more and preferably up to 50, up to 45, up to 40, up to 35 or up to 30 amino acids. Preferably the linker is enriched in glycine and/or serine amino acids. Preferably, at least 50%, at least 60%, at least 70%, at least 80%, at least 90%, or at least 95% of the amino acids of the linker are glycine and/or serine. In one preferred embodiment, a linker is substantially composed of the amino acids glycine and serine. In one embodiment, the linker comprises the amino acid sequence $(GGS)_a(GSS)_b(GGG)_c(SSG)_d(GSG)_e$ wherein a, b, c, d and e is independently a number selected from 0, 1, 2, 3, 4, 5, 6, 7, 8, 9, 10, 11, 12, 13, 14, 15, 16, 17, 18, 19, or 20 and wherein a+b+c+d+e are different from 0 and preferably are 2 or more, 3 or more, 4 or more or 5 or more. In one embodiment, the linker comprises a sequence as described herein including the linker sequences described in the examples such as the sequence GGSGGGGSG.

In one particularly preferred embodiment, a polypeptide incorporating one or more neo-epitopes such as a polyepitopic polypeptide according to the present invention is administered to a patient in the form of a nucleic acid, preferably RNA such as in vitro transcribed or synthetic RNA, which may be expressed in cells of a patient such as antigen presenting cells to produce the polypeptide. The present invention also envisions the administration of one or more multiepitopic polypeptides which for the purpose of the present invention are comprised by the term "polyepitopic polypeptide", preferably in the form of a nucleic acid, preferably RNA such as in vitro transcribed or synthetic RNA, which may be expressed in cells of a patient such as antigen presenting cells to produce the one or more polypeptides. In the case of an administration of more than one multiepitopic polypeptide the neo-epitopes provided by the different multiepitopic polypeptides may be different or partially overlapping. Once present in cells of a patient such as antigen presenting cells the polypeptide according to the invention is processed to produce the neo-epitopes identified according to the invention. Administration of a vaccine provided according to the invention preferably provides MHC class I-presented epitopes that are capable of eliciting a CD8+ helper T cell response against cells expressing antigens from which the MHC presented epitopes are derived. Administration of a vaccine provided according to the invention may also provide MHC class II-presented epitopes that are capable of eliciting a CD4+ T cell response against cells expressing antigens from which the MHC presented epitopes are derived. Furthermore, administration of a vaccine provided according to the invention may provide one or more neo-epitopes (including known neo-epitopes and neo-epitopes identified according to the invention) as well as one or more epitopes not containing cancer specific somatic mutations but being expressed by cancer cells and preferably inducing an immune response against cancer cells, preferably a cancer specific immune response.

The vaccine provided according to the invention may be a recombinant vaccine.

The term "recombinant" in the context of the present invention means "made through genetic engineering". Preferably, a "recombinant entity" such as a recombinant polypeptide in the context of the present invention is not occurring naturally, and preferably is a result of a combination of entities such as amino acid or nucleic acid sequences which are not combined in nature. For example, a recombinant polypeptide in the context of the present invention may contain several amino acid sequences such as neo-epitopes or vaccine sequences derived from different proteins or different portions of the same protein fused together, e.g., by peptide bonds or appropriate linkers.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring.

The agents and compositions described herein can be used to treat a subject with a disease, e.g., a disease characterized by the presence of diseased cells expressing an antigen and presenting a fragment thereof. Particularly preferred diseases are cancer diseases. Agents and compositions described herein may also be used for immunization or vaccination to prevent a disease described herein.

The term "disease" refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases. In humans, "disease" is often used more broadly to refer to any condition that causes pain, dysfunction, distress, social problems, or death to the individual afflicted, or similar problems for those in contact with the individual. In this broader sense, it sometimes includes injuries, disabilities, disorders, syndromes, infections, isolated symptoms, deviant behaviors, and atypical variations of structure and function, while in other contexts and for other purposes these may be considered distinguishable categories. Diseases usually affect individuals not only physically, but also emotionally, as contracting and living with many diseases can alter one's perspective on life, and one's personality.

The term "normal" refers to the healthy state or the conditions in a healthy subject or tissue, i.e., non-pathological conditions, wherein "healthy" preferably means non-cancerous.

The term "disease associated with an antigen" or "disease involving an antigen" refers to any disease which implicates an antigen, e.g. a disease which is characterized by the presence of an antigen or cells expressing an antigen. The disease involving an antigen can be an infectious disease, an autoimmune disease, or a cancer disease or simply cancer. As mentioned above, the antigen may be a disease-associated antigen, such as a tumor-associated antigen, a viral antigen, or a bacterial antigen.

"Disease involving cells expressing an antigen" means according to the invention that expression of the antigen in cells of a diseased tissue or organ is detected. Expression in cells of a diseased tissue or organ may be increased compared to the state in a healthy tissue or organ. An increase refers to an increase by at least 10%, in particular at least 20%, at least 50%, at least 100%, at least 200%, at least 500%, at least 1000%, at least 10000% or even more. In one embodiment, expression is only found in a diseased tissue, while expression in a healthy tissue is repressed. According to the invention, diseases involving or being associated with cells expressing an antigen include cancer diseases.

The term "infectious disease" refers to any disease which can be transmitted from individual to individual or from organism to organism, and is caused by a microbial agent (e.g. common cold). Infectious diseases are known in the art and include, for example, a viral disease, a bacterial disease, or a parasitic disease, which diseases are caused by a virus, a bacterium, and a parasite, respectively. In this regard, the infectious disease can be, for example, hepatitis, sexually transmitted diseases (e.g. chlamydia or gonorrhea), tuberculosis, HIV/acquired immune deficiency syndrome (AIDS), diphtheria, hepatitis B, hepatitis C, cholera, severe acute respiratory syndrome (SARS), the bird flu, and influenza.

The term "autoimmune disease" refers to any disease in which the body produces an immunogenic (i.e. immune system) response to some constituent of its own tissue. In other words, the immune system loses its ability to recognize some tissue or system within the body as self and targets and attacks it as if it were foreign. Autoimmune diseases can be classified into those in which predominantly one organ is affected (e.g. hemolytic anemia and anti-immune thyroiditis), and those in which the autoimmune disease process is diffused through many tissues (e.g. systemic lupus erythematosus). For example, multiple sclerosis is thought to be caused by T cells attacking the sheaths that surround the nerve fibers of the brain and spinal cord. This results in loss of coordination, weakness, and blurred vision. Autoimmune diseases are known in the art and include, for instance, Hashimoto's thyroiditis, Grave's disease, lupus, multiple sclerosis, rheumatic arthritis, hemolytic anemia, anti-immune thyroiditis, systemic lupus erythematosus, celiac disease, Crohn's disease, colitis, diabetes, scleroderma, psoriasis, and the like.

The terms "cancer disease" or "cancer" refer to or describe the physiological condition in an individual that is typically characterized by unregulated cell growth. Examples of cancers include, but are not limited to, carcinoma, lymphoma, blastoma, sarcoma, and leukemia. More particularly, examples of such cancers include bone cancer, blood cancer lung cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma. The term "cancer" according to the invention also comprises cancer metastases.

According to the invention, the term "tumor" or "tumor disease" refers to an abnormal growth of cells (called neoplastic cells, tumorigenous cells or tumor cells) preferably forming a swelling or lesion. By "tumor cell" is meant an abnormal cell that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign, pre-malignant or malignant.

For purposes of the present invention, the terms "cancer" and "cancer disease" are used interchangeably with the terms "tumor" and "tumor disease".

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor, i.e. a secondary tumor or metastatic tumor, at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system.

The cells of a secondary or metastatic tumor are like those in the original tumor. This means, for example, that, if ovarian cancer metastasizes to the liver, the secondary tumor is made up of abnormal ovarian cells, not of abnormal liver cells. The tumor in the liver is then called metastatic ovarian cancer, not liver cancer.

The term "circulating tumor cells" or "CTCs" relates to cells that have detached from a primary tumor or tumor metastases and circulate in the bloodstream. CTCs may constitute seeds for subsequent growth of additional tumors (metastasis) in different tissues. Circulating tumor cells are found in frequencies in the order of 1-10 CTC per mL of whole blood in patients with metastatic disease. Research methods have been developed to isolate CTC. Several research methods have been described in the art to isolate CTCs, e.g. techniques which use of the fact that epithelial cells commonly express the cell adhesion protein EpCAM, which is absent in normal blood cells. Immunomagnetic bead-based capture involves treating blood specimens with antibody to EpCAM that has been conjugated with magnetic particles, followed by separation of tagged cells in a magnetic field. Isolated cells are then stained with antibody to another epithelial marker, cytokeratin, as well as a common leukocyte marker CD45, so as to distinguish rare CTCs from contaminating white blood cells. This robust and semi-automated approach identifies CTCs with an average yield of approximately 1 CTC/mL and a purity of 0.1% (Allard et al., 2004: *Clin Cancer Res* 10, 6897-6904). A second method for isolating CTCs uses a microfluidic-based CTC capture device which involves flowing whole blood through a chamber embedded with 80,000 microposts that have been rendered functional by coating with antibody to EpCAM. CTCs are then stained with secondary antibodies against either cytokeratin or tissue specific markers, such as PSA in prostate cancer or HER2 in breast cancer and are visualized by automated scanning of microposts in multiple planes along three dimensional coordinates. CTC-chips are able to identifying cytokerating-positive circulating tumor cells in patients with a median yield of 50 cells/ml and purity ranging from 1-80% (Nagrath et al., 2007: *Nature* 450, 1235-1239). Another possibility for isolating CTCs is using the CellSearch™ Circulating Tumor Cell (CTC) Test from Veridex, LLC (Raritan, NJ) which captures, identifies, and counts CTCs in a tube of blood. The CellSearch™ system is a U.S. Food and Drug Administration (FDA) approved methodology for enumeration of CTC in whole blood which is based on a combination of immunomagnetic labeling and automated digital microscopy. There are other methods for isolating CTCs described in the literature all of which can be used in conjunction with the present invention.

A relapse or recurrence occurs when a person is affected again by a condition that affected them in the past. For example, if a patient has suffered from a tumor disease, has received a successful treatment of said disease and again develops said disease said newly developed disease may be considered as relapse or recurrence. However, according to the invention, a relapse or recurrence of a tumor disease may but does not necessarily occur at the site of the original tumor disease. Thus, for example, if a patient has suffered from ovarian tumor and has received a successful treatment a relapse or recurrence may be the occurrence of an ovarian tumor or the occurrence of a tumor at a site different to ovary. A relapse or recurrence of a tumor also includes situations wherein a tumor occurs at a site different to the site of the original tumor as well as at the site of the original tumor. Preferably, the original tumor for which the patient has received a treatment is a primary tumor and the tumor at a site different to the site of the original tumor is a secondary or metastatic tumor.

The term "immunotherapy" relates to the treatment of a disease or condition by inducing, enhancing, or suppressing an immune response. Immunotherapies designed to elicit or amplify an immune response are classified as activation immunotherapies, while immunotherapies that reduce or suppress an immune response are classified as suppression immunotherapies. The term "immunotherapy" includes antigen immunization or antigen vaccination, or tumor immunization or tumor vaccination. The term "immunotherapy" also relates to the manipulation of immune responses such that inappropriate immune responses are modulated into more appropriate ones in the context of autoimmune diseases such as rheumatic arthritis, allergies, diabetes or multiple sclerosis.

The terms "immunization" or "vaccination" describe the process of administering an antigen to an individual with the purpose of inducing an immune response, for example, for therapeutic or prophylactic reasons.

The term "therapeutic treatment" or simply "treatment" relates to any treatment which improves the health status and/or prolongs (increases) the lifespan of an individual. Said treatment may eliminate the disease in an individual, arrest or slow the development of a disease in an individual, inhibit or slow the development of a disease in an individual, decrease the frequency or severity of symptoms in an individual, and/or decrease the recurrence in an individual who currently has or who previously has had a disease.

The term "prophylactic treatment" or "preventive treatment" relates to any treatment that is intended to prevent a disease from occurring in an individual. The terms "prophylactic treatment" or "preventive treatment" are used herein interchangeably.

The terms "protect", "prevent", "prophylactic", "preventive", or "protective" relate to the prevention and/or treatment of the occurrence and/or the propagation of a disease, e.g. tumor, in an individual. For example, a prophylactic administration of an immunotherapy, e.g. by administering a composition described herein, can protect the receiving individual from the development of a tumor. For example, a therapeutic administration of an immunotherapy, e.g. by administering a composition described herein, can stop the development of a disease, e.g. lead to the inhibition of the progress/growth of a tumor. This comprises the deceleration of the progress/growth of the tumor, in particular a disruption of the progression of the tumor, which preferably leads to elimination of the tumor. A therapeutic administration of an immunotherapy may protect the individual, for example, from the dissemination or metastasis of existing tumors.

The term "individual" or "subject" relates to vertebrates, particularly mammals. For example, mammals in the context of the present invention are humans, non-human primates, domesticated mammals such as dogs, cats, sheep, cattle, goats, pigs, horses etc., laboratory animals such as mice, rats, rabbits, guinea pigs, etc. as well as animals in captivity such as animals of zoos. The term "subject" also relates to non-mammalian vertebrates such as birds (particularly domesticated birds such as chicken, ducks, geese, turkeys) and to fish (particularly farmed fish, e.g. salmon or catfish). The term "animal" as used herein also includes humans. Preferably, the term "patient" relates to a diseased individual.

The agents described herein may be administered in the form of any suitable pharmaceutical composition. The term "pharmaceutical composition" relates to a formulation comprising a therapeutically effective agent or a salt thereof, preferably together with pharmaceutical excipients such as buffers, preservatives and tonicity modifiers. Said pharmaceutical composition is useful for treating, preventing, or reducing the severity of a disease or disorder by administration of said pharmaceutical composition to an individual. A pharmaceutical composition is also known in the art as a pharmaceutical formulation. The pharmaceutical composition can be administered locally or systemically.

The term "systemic administration" refers to the administration of a therapeutically effective agent such that the agent becomes widely distributed in the body of an individual in significant amounts and develops a biological effect. According to the present invention, it is preferred that administration is by parenteral administration.

The term "parenteral administration" refers to administration of a therapeutically effective agent such that the agent does not pass the intestine. The term "parenteral administration" includes intravenous administration, subcutaneous administration, intradermal administration or intraarterial administration but is not limited thereto.

In one particularly preferred embodiment, the composition according to the present invention is administered to muscle tissue, such as skeletal muscle. Intramuscular administration such as by intramuscular injection thus is the preferred route of administration.

Administration can be achieved in various ways. In one embodiment, the composition according to the present invention is administered by injection. In a preferred embodiment, injection is via a needle. Needle-free injection may be used as an alternative.

The pharmaceutical compositions of the present invention may comprise at least one adjuvant. The term "adjuvant" relates to compounds, which when administered in combination with an antigen or antigen peptide to an individual, prolong or enhance or accelerate an immune response. It is assumed that adjuvants exert their biological activity by one or more mechanisms, including an increase of the surface of the antigen, a prolongation of the retention of the antigen in the body, a retardation of the antigen release, targeting of the antigen to macrophages, increase of the uptake of the antigen, enhancement of antigen processing, stimulation of cytokine release, stimulation and activation of immune cells such as B cells, macrophages, dendritic cells, T cells and unspecific activation of immune cells. Adjuvants comprise a heterogeneous group of compounds such as oil emulsions (e.g., Freund's adjuvants), mineral compounds (such as alum), bacterial products (such as *Bordetella pertussis* toxin), or immune-stimulating complexes. Examples for adjuvants include saponins, incomplete Freund's adjuvants, complete Freund's adjuvants, tocopherol or alum, but are not limited thereto.

The pharmaceutical composition according to the present invention is generally applied in a "pharmaceutically effective amount" and in "a pharmaceutically acceptable preparation".

The term "pharmaceutically effective amount" refers to the amount which achieves a desired reaction or a desired effect alone or together with further doses. In the case of the treatment of a particular disease, the desired reaction preferably relates to inhibition of the course of the disease. This comprises slowing down the progress of the disease and, in particular, interrupting or reversing the progress of the disease. The desired reaction in a treatment of a disease may also be delay of the onset or a prevention of the onset of said disease or said condition. An effective amount of the compositions described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the compositions described herein may depend on various of such parameters. In the case that a reaction in a patient is insufficient with an initial dose, higher doses (or effectively higher doses achieved by a different, more localized route of administration) may be used.

The term "pharmaceutically acceptable" refers to the non-toxicity of a material which does not interact with the action of the active component of the pharmaceutical composition.

The pharmaceutical compositions of the present invention may contain salts, buffers, preserving agents, carriers and optionally other therapeutic agents. Preferably, the pharmaceutical compositions of the present invention comprise one or more pharmaceutically acceptable carriers, diluents and/or excipients.

The term "excipient" is intended to indicate all substances in a pharmaceutical composition which are not active ingredients such as binders, lubricants, thickeners, surface active agents, preservatives, emulsifiers, buffers, flavoring agents, or colorants.

The term "diluent" relates a diluting and/or thinning agent. Moreover, the term "diluent" includes any one or more of fluid, liquid or solid suspension and/or mixing media.

The term "carrier" relates to one or more compatible solid or liquid fillers or diluents, which are suitable for an administration to a human. The term "carrier" relates to a natural or synthetic organic or inorganic component which is combined with an active component in order to facilitate the application of the active component. Preferably, carrier components are sterile liquids such as water or oils, including those which are derived from mineral oil, animals, or plants, such as peanut oil, soy bean oil, sesame oil, sunflower oil, etc. Salt solutions and aqueous dextrose and glycerin solutions may also be used as aqueous carrier compounds.

Pharmaceutically acceptable carriers or diluents for therapeutic use are well known in the pharmaceutical art, and are described, for example, in Remington's Pharmaceutical Sciences, Mack Publishing Co. (A. R Gennaro edit. 1985). Examples of suitable carriers include, for example, magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Examples of suitable diluents include ethanol, glycerol and water.

Pharmaceutical carriers, excipients or diluents can be selected with regard to the intended route of administration and standard pharmaceutical practice. The pharmaceutical compositions of the present invention may comprise as, or in addition to, the carrier(s), excipient(s) or diluent(s) any suitable binder(s), lubricant(s), suspending agent(s), coating agent(s), and/or solubilising agent(s). Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like. Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

In one embodiment, the composition is an aqueous composition. The aqueous composition may optionally comprise solutes, e.g. salts. In one embodiment, the composition is in the form of a freeze-dried composition. A freeze-dried composition is obtainable by freeze-drying a respective aqueous composition.

The agents and compositions provided herein may be used alone or in combination with other therapeutic regimens such as surgery, irradiation, chemotherapy and/or bone marrow transplantation (autologous, syngeneic, allogeneic or unrelated).

The present invention is described in detail and is illustrated by the figures and examples, which are used only for illustration purposes and are not meant to be limiting. Owing to the description and the examples, further embodiments which are likewise included in the invention are accessible to the skilled worker.

FIGURES

FIG. 1. The proteins of published epitopes are significantly enriched in exosomes and the cytosol if compared to random peptides (proteome).

Figure 2:
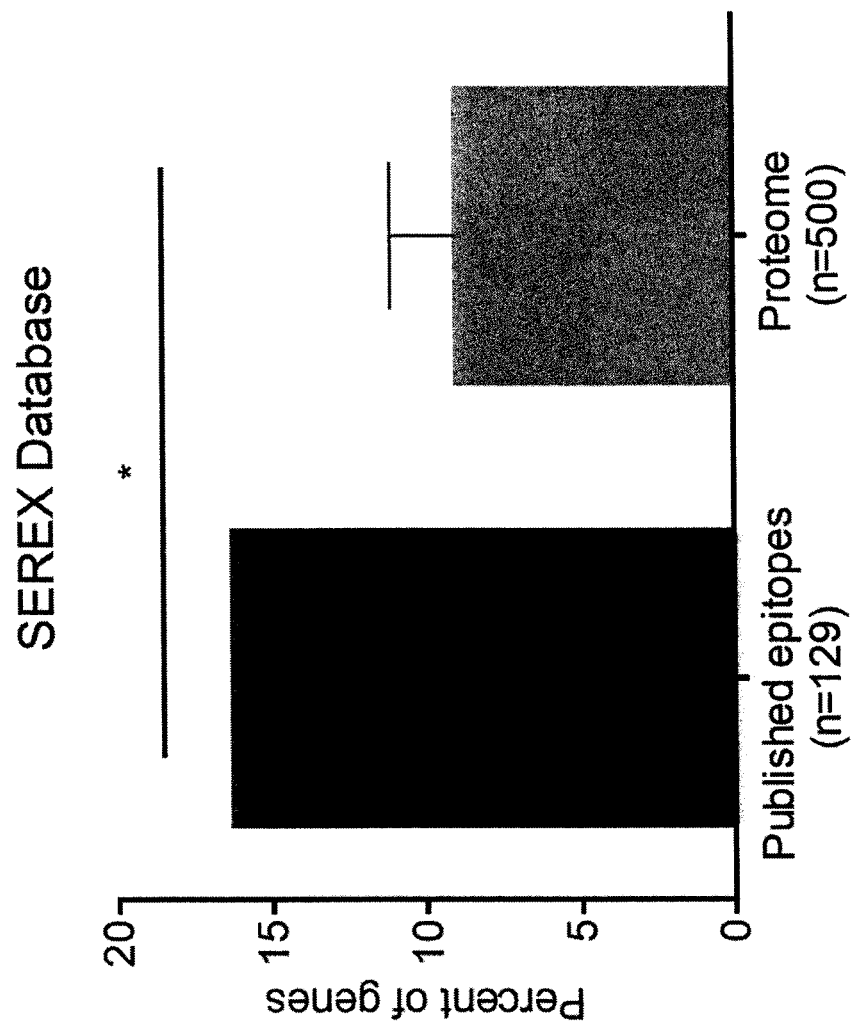

FIG. 2. Genes of published epitopes are significantly more often found in the SEREX Database compared to random peptides.

EXAMPLES

The techniques and methods used herein are described herein or carried out in a manner known per se and as described, for example, in Sambrook et al., Molecular Cloning: A Laboratory Manual, $2^{nd}$ Edition (1989) Cold Spring Harbor Laboratory Press, Cold Spring Harbor, N.Y. All methods including the use of kits and reagents are carried out according to the manufacturers' information unless specifically indicated.

Example 1: Location of Proteins Containing Published Epitopes

The literature was screened in order to identify MHC class I-restricted, mutated neo-epitopes ("Published epitopes", n=129) and their location was compared to a random sample of protein coding genes ("Proteome", n=500) (FIG. 1). The location of the respective genes was determined via the gene ontology database (ebi.ac.uk/QuickGO/). Moreover, presence in exosomes was tested via the ExoCarta database (exocarta.org/). As shown in FIG. 1, neo-epitope containing genes are significantly enriched in exosomes as well as in the cytosol compared to the control genes (fishers exact test; p<0.0001).

In a second step, the presence of genes from published epitopes in the SEREX database (V. Jongeneel, Cancer Immunity, Vol. 1, p. 3 (30 Mar. 2001)) was compared to the random control genes (FIG. 2). The SEREX database lists proteins that were shown to be recognized by autoantibodies. Genes of published epitopes were significantly more often found in the SEREX database compared to random peptides (fishers exact test; p<0.0001).

The results shown in FIGS. 1 and 2 indicate that presence of mutated genes in exosomes, the cytosol or an autoantibody database are useful parameters to predict relevant mutated antigens for immunotherapy.

The invention claimed is:

1. A method for making a cancer vaccine, the method comprising:
   determining subcellular distribution or localization of a cancer-associated neo-antigen expressed by cancer cells or neo-epitope thereof comprising one or more cancer-specific amino acid modifications;
   selecting, for inclusion in a cancer vaccine, the cancer-associated neo-antigen expressed by cancer cells or neo-epitope thereof comprising one or more cancer-specific amino acid modifications when the cancer-associated neo-antigen or neo-epitope, or genetic material that encodes it, is determined to be abundant in the cytosol of cancer cells, and/or within and/or on the surface of exosomes therefrom; and
   manufacturing a cancer vaccine, or having a cancer vaccine be manufactured, that includes the selected cancer-associated neo-antigen or neo-epitope thereof, or a-nucleic acid encoding it.

2. The method of claim 1, wherein the selecting comprises determining that the cancer-associated neo-antigen or neo-epitope thereof is present, in an MHC peptide complex, within exosomes and/or on the surface of the exosomes.

3. The method of claim 1, wherein the cancer-specific amino acid modification comprises a cancer-specific disease-specific somatic mutation.

4. The method of claim 1, wherein the cancer-associated neo-antigen or neo-epitope thereof is or comprises an MHC binding peptide.

5. The method of claim 1, wherein the determining comprises determining subcellular distribution or localization of at least two cancer-associated neo-antigens or neo-epitopes thereof comprising one or more cancer-specific amino acid modifications.

6. The method of claim 5, further comprising determining that the cancer-specific amino acid modification is part of an MHC binding peptide.

7. The method of claim 1, further comprising administering the cancer vaccine to an individual with the cancer cells.

8. The method of claim 1, wherein the determining comprises accessing at least one database that includes subcellular localization data for a plurality of proteins in a proteome to determine subcellular distribution or localization of the cancer-associated neo-antigen or neo-epitope thereof.

9. The method of claim 1, wherein abundance of the cancer-associated neo-antigen or neo-epitope thereof, or genetic material that encodes it, in the cytosol indicates processing and presentation of the neo-antigen or neo-epitope thereof via the MHC I pathway of cancer cells.

10. The method of claim 9, wherein processing and presentation of the cancer-associated neo-antigen or neo-epitope thereof via the MHC I pathway results in recognition of complexes formed by MHC I and cancer-associated neo-antigen or neo-epitope thereof by CD8+ T cells.

11. The method of claim 1, wherein abundance of the cancer-associated neo-antigen or neo-epitope thereof, or genetic material that encodes it, within and/or on the surface of exosomes indicates accumulation of the cancer-associated neo-antigen or neo-epitope thereof, or genetic material that encodes it, in antigen presenting cells.

12. The method of claim 11, wherein the antigen presenting cells are or comprise professional antigen presenting cells.

13. The method of claim 11, wherein accumulation of the cancer-associated neo-antigen or neo-epitope thereof, or genetic material that encodes it, in antigen presenting cells indicates processing and presentation of the cancer-associated neo-antigen or neo-epitope thereof via the MHC I and/or MHC II pathway of the antigen presenting cells.

14. The method of claim 13, wherein processing and presentation of the cancer-associated neo-antigen or neo-epitope thereof via the MHC I pathway results in recognition of complexes formed by MHC I and cancer-associated neo-antigen or neo-epitope thereof by CD8+ T cells.

15. The method of claim 1, wherein the determining ascertains that the cancer-associated neo-antigen or neo-epitope, or genetic material that encodes it, is abundant in the cytosol of cancer cells.

16. The method of claim 1, wherein the determining ascertains that the cancer-associated neo-antigen or neo-epitope, or genetic material that encodes it, is abundant within and/or on the surface of exosomes from cancer cells.

17. The method of claim 1, wherein the determining ascertains that the cancer-associated neo-antigen or neo-epitope, or genetic material that encodes it, is enriched in the cytosol of cancer cells, or within and/or on the surface of exosomes therefrom relative to a reference set of peptides representative of the proteome.

18. The method of claim 17, wherein the determining ascertains that the cancer-associated neo-antigen or neo-epitope, or genetic material that encodes it, is enriched within and/or on the surface of exosomes as well as in the cytosol relative to the reference set of peptides.

19. A method for producing a vaccine that upon administration to individuals with cancer cells induces an immune response against the cancer cells, the method comprising:
identifying cancer-associated neo-antigens expressed by cancer cells or neo-epitopes thereof comprising one or more cancer-specific amino acid modifications, or genes encoding them;
determining subcellular distribution and/or localization of the cancer-associated neo-antigens or neo-epitopes thereof, or genetic material that encodes them, in the cancer cells;
selecting, for inclusion in a cancer vaccine, at least one of the cancer-associated neo-antigens or neo-epitopes thereof when the cancer-associated neo-antigen or neo-epitope, or genetic material that encodes it, is determined to be abundant in cytosol of cancer cells, and/or within and/or on the surface of exosomes from the cancer cells; and
producing a vaccine, or having a vaccine be produced, for administration to individuals with the cancer cells, wherein the vaccine comprises the selected at least one cancer-associated neo-antigen or neo-epitope thereof, or a nucleic acid encoding it.

\* \* \* \* \*